US010886761B1

(12) United States Patent
Schobben et al.

(10) Patent No.: US 10,886,761 B1
(45) Date of Patent: Jan. 5, 2021

(54) MOBILE PHONE COVER COMPRISING TWO OR MORE CHARGING STATIONS FOR RECHARGEABLE INSTRUMENTS

(71) Applicant: Salvia BioElectronics B.V., Eindhoven (NL)

(72) Inventors: Daniël Willem Elisabeth Schobben, Eindhoven (NL); Hubert Cécile François Martens, Eindhoven (NL); Marjolein Wilhelmina Maria Schets, Eindhoven (NL)

(73) Assignee: Salvia BioElectronics B.V.

( * ) Notice: Subject to any disclaimer, the term of this patent is extended or adjusted under 35 U.S.C. 154(b) by 0 days.

(21) Appl. No.: 16/704,306

(22) Filed: Dec. 5, 2019

(51) Int. Cl.
*H04M 1/00* (2006.01)
*H02J 7/00* (2006.01)
(Continued)

(52) U.S. Cl.
CPC ........ *H02J 7/0044* (2013.01); *A61N 1/36075* (2013.01); *A61N 1/3787* (2013.01); *H02J 50/12* (2016.02); *H04B 1/3888* (2013.01)

(58) Field of Classification Search
CPC .... H02J 7/0044; H02J 50/12; A61N 1/36075; A61N 1/3787; H04B 1/3888
(Continued)

(56) References Cited

U.S. PATENT DOCUMENTS 8,891,800 B1 * 11/2014 Shaffer ................ H04R 1/1025
381/384
9,116,665 B2 * 8/2015 Su ......................... G06F 1/1628
(Continued)

FOREIGN PATENT DOCUMENTS

WO 2009112976 A1 9/2009
WO 2017120357 A1 7/2017

OTHER PUBLICATIONS

Hassler, Boretius, Steglitz, Polymers for neural implants, Journal of Polymer Science Part B: Polymer Physics/vol. 49, Iss. 1, Nov. 23, 2010, online, 10.1002/polb.22169.

*Primary Examiner* — Sonny Trinh
(74) *Attorney, Agent, or Firm* — Fresh IP PLC; Clifford D. Hyra; Aubrey Y. Chen

(57) ABSTRACT

A mobile phone cover is provided comprising: a holder 120, 1120, 2120, 3120 for receiving and retaining a mobile phone 108, the mobile phone comprising an energy supply; a portable charging device 106, 1106, 2106, 3106 having two or more charging stations 110, 1110, 2110, 3110, each charging station 110, 1110, 2110, 3110 being configured and arranged for receiving and retaining a rechargeable instrument 104, the rechargeable instrument 104 comprising an energy storage; the portable charging device 106, 1106, 2106, 3106 being further configured and arranged: to transfer energy, in use, from the energy supply of the mobile phone 108, placed in the holder, to the two or more charging stations 110, 1110, 2110, 3110; and to transfer energy, in use, from the charging stations 110, 1110, 2110, 3110 to the energy storage of the rechargeable instrument 104 placed in the respective charging station 110, 1110, 2110, 3110.

By providing a portable charging device in a mobile phone case, there is a reduced risk that an instrument will not work properly or be inoperable. There may also be lower chance that the user will forget to take the rechargeable instruments when they are travelling and/or away from home.

30 Claims, 13 Drawing Sheets

(51) Int. Cl.
*H04B 1/3888* (2015.01)
*A61N 1/36* (2006.01)
*A61N 1/378* (2006.01)
*H02J 50/12* (2016.01)

(58) Field of Classification Search
USPC .......................................... 455/575.1, 575.8
See application file for complete search history.

(56) References Cited

U.S. PATENT DOCUMENTS

| | | |
|---|---|---|
| 9,602,907 B2 * | 3/2017 | Shaffer ................ H04R 1/1025 |
| 10,442,601 B1 | 10/2019 | Al-Johany |
| 10,616,386 B2 * | 4/2020 | Lee .................... H01M 2/1055 |
| 2007/0073356 A1 | 3/2007 | Rooney |
| 2008/0125164 A1 * | 5/2008 | Singh .................. H04M 1/0258 |
| | | 455/550.1 |
| 2008/0143954 A1 | 6/2008 | Abreu |
| 2010/0057165 A1 | 3/2010 | Moffitt |
| 2011/0093043 A1 | 4/2011 | Torgerson |
| 2016/0166828 A1 | 6/2016 | Yu |
| 2017/0072200 A1 | 3/2017 | Fletcher et al. |
| 2018/0093096 A1 | 4/2018 | Mashiach |
| 2018/0117332 A1 | 5/2018 | Robinson |
| 2018/0262826 A1 * | 9/2018 | Ingram ................ H04R 1/1016 |

* cited by examiner

US 10,886,761 B1

MOBILE PHONE COVER COMPRISING TWO OR MORE CHARGING STATIONS FOR RECHARGEABLE INSTRUMENTS

TECHNICAL FIELD

This disclosure relates to a mobile phone cover comprising a mobile phone holder and two or more charging stations for receiving and retaining rechargeable instruments. It further relates to a medical system comprising N implantable medical devices (IMD), a mobile phone cover, and M rechargeable instruments, wherein M≥N≥2, a rechargeable instrument being configured for powering wirelessly an implantable medical device (IMD).

BACKGROUND ART

Neurostimulation systems comprising implantable neurostimulation leads are used to treat chronic pain. Conventional implantable spinal cord stimulation leads are designed for placement in the spinal canal as part of a spinal cord stimulation system, and for the therapeutic purpose of treating various forms of chronic back and extremity pain.

A neurostimulation system for the purpose of treating chronic headaches is known from WO2017/120357A1. The system includes N implantable pulse generators (IPGs) from which multiple stimulating leads may extend sufficiently to allow for adequate stimulation over multiple regions of the head and an external charge transfer system. One external charge transfer system (ECTS) is configured to charge and to communicate with the N IPGs via N series-connected charge transfer coils. Each of the receive coils of an IPG is tuned to the resonant frequency of the respective charge transfer coil. By sending forward telemetry commands instructing a selected IPG to communicate back telemetry data to the ECTS, the non-selected IPG will forego attempted back telemetry during such times.

By using an external charge transfer system outside a dermis layer, the degree of access to the controller is greatly increased, and in some cases, the functionality that needs to be implanted may be reduced in some cases. However, the system may only be operated optimally if the external charge transfer system is correctly configured and fully operational. In addition, when using external units, it may not be possible to operate an implant correctly if the external unit is not present or it is malfunctioning. In some cases, it may not be possible to operate an implant at all with a missing or defective external unit.

SUMMARY OF INVENTION

It is an objective of the present technology to provide a portable charging device for rechargeable instruments that increases the chance that operable instruments will be available to a user.

In many applications where rechargeable instruments are used, common problems including the user forgetting to recharge the instruments and/or the user having too little time to fully recharge the instruments. Especially where the rechargeable instruments are used for a personalized application, such as a personalised therapeutic, stimulation or medical use, users become more reliant and dependent on the correct operation of these instruments, resulting in a severe inconvenience if they are not sufficiently charged. These issues are particularly prominent when the battery lifetime of the rechargeable instruments is less than a day, and require intermediate charging. Carrying specific charging means daily is a burden and may not be consequently done by the user, leading to major discomfort when the instruments run out of power.

By providing a portable charging device in a mobile phone case, there is a reduced risk that an instrument will not work properly or be inoperable. There may also be lower chance that the user will forget to take the rechargeable instruments when they are travelling and/or away from home.

Preferred dimensions for the mobile phone cover are those suitable for transport in a small bag, and most preferably pocket-sized.

Smaller dimensions should preferably be used, as this may increase portability and may increase the likelihood that the user will use the cover regularly, preferably every day.

The mobile phone cover described herein is highly configurable—differently dimensioned covers may be provided for one or more specific type of phone, or a more universal mobile phone cover may be provided to receive and retain a wide range of mobile phones.

In a further aspect, the mobile phone cover may be modified to provide inconspicuous and unobtrusive storage and charging. In particular, when the rechargeable instruments are configured for one or more therapeutic, stimulation and/or medical uses, the user may not wish others to be aware that they have a condition which requires treatment.

BRIEF DESCRIPTION OF THE DRAWINGS

These and other aspects, properties and advantages will be explained hereinafter based on the following description with reference to the drawings, wherein like reference numerals denote like or comparable parts, and in which.

DETAILED DESCRIPTION OF INVENTION

Figure 1:
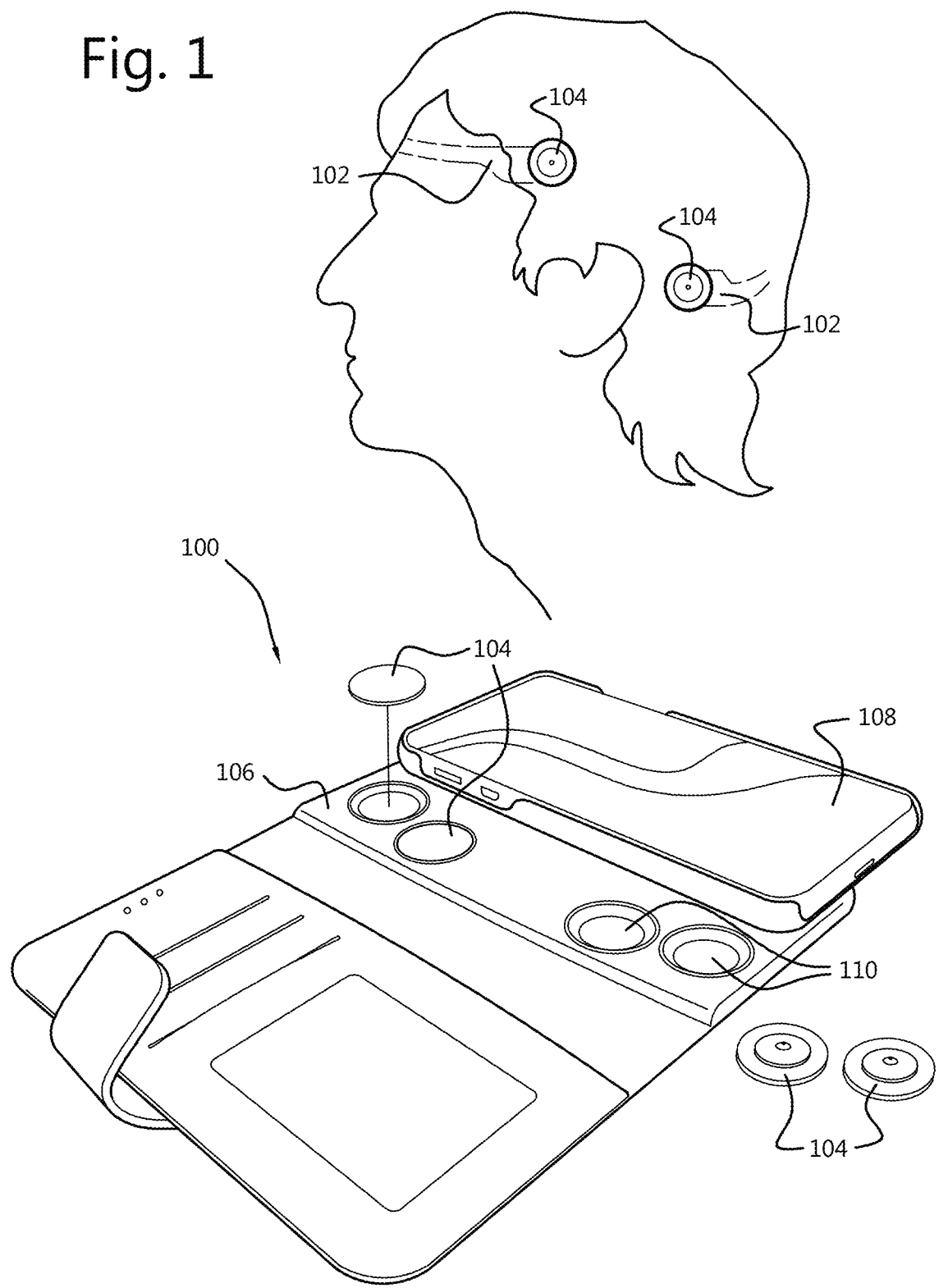
FIG. 1 shows schematically the components of a neurostimulation system.
Figure 8:
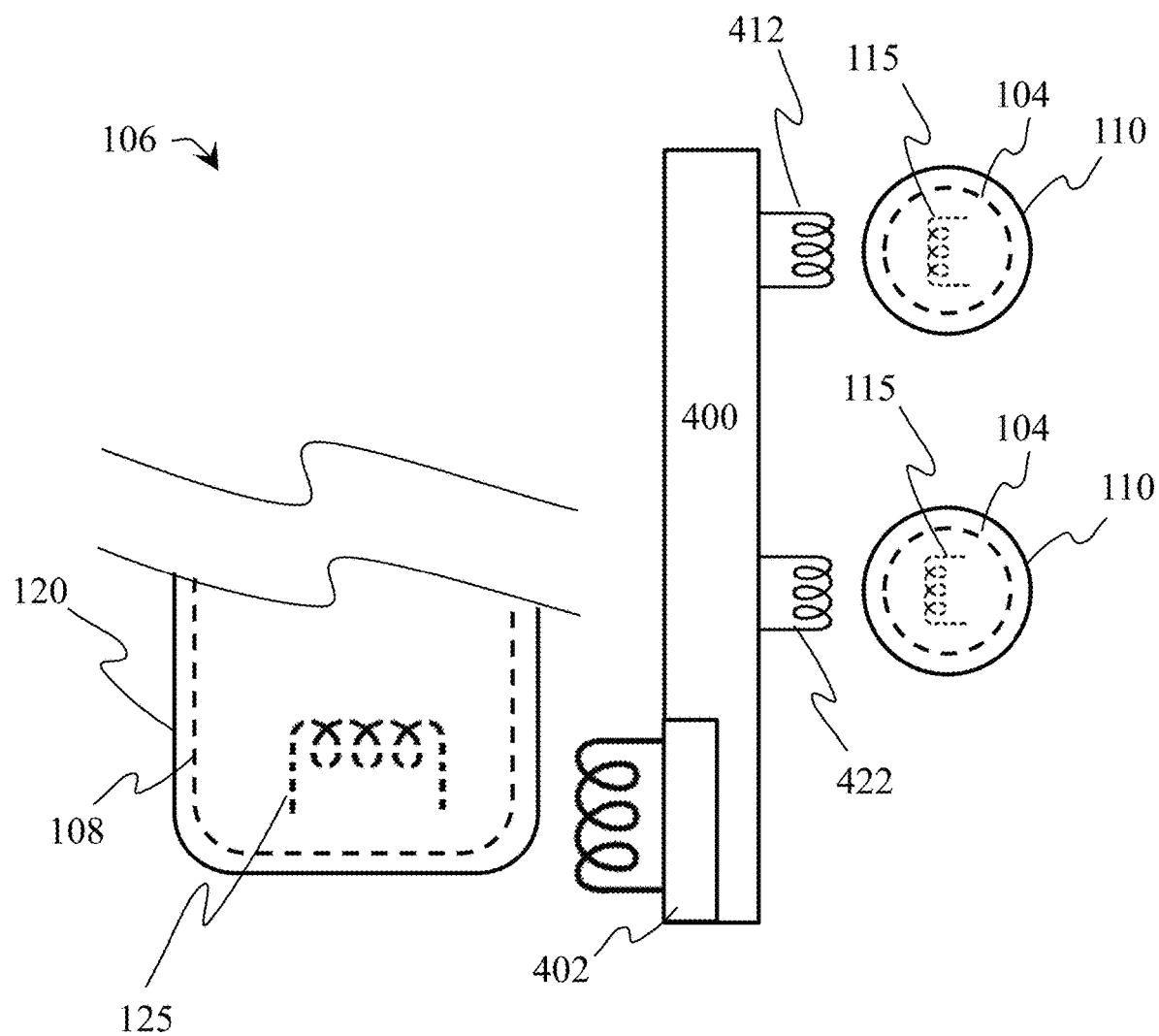
FIG. 8 schematically depicts a charging system.

FIG. 1 shows schematically the components of a neurostimulation system according to the present subject technology and FIG. 8 schematically depicts an example of a charging system comprised in a mobile device cover. The neurostimulation system is designed for the treatment of chronic headaches. It incorporates multiple elements and features that consider the unique anatomic, physiologic, and other related challenges of treating pain with implantable neurostimulation, thereby greatly improving on therapeutic response, patient safety, medical risk, and medical costs, thereby providing an improved overall patient satisfaction.

The neurostimulation system comprises four different components: an implantable medical device (IMD) 102, a rechargeable instrument 104, such as an external power transfer device (EPTD) 104, a charging device 106, and a mobile phone 108. FIG. 1 shows two IMDs 102; an Occipital Nerve Stimulation (ONS) implant and a Supra-Orbital Nerve Stimulation (SONS) implant. The ONS implant is implanted underneath the skin of the back of the head. The ONS implant stimulates the peripheral nerves using mild electrical pulses. This treatment is used to lower the intensity and frequency of headache attacks. The SONS implant is placed underneath the skin of the forehead and during stimulation an electrical current is applied to the supraorbital nerves, a branch of the frontal nerve.

The EPTD 104 powers wirelessly the IMD 102 and it may be mechanically coupled to the IMD by means of magnetic forces. In an embodiment, the IMD comprises an internal magnet and the EPTD comprises an external magnet. In the context of the present description the term "internal" means in the head underneath the skin and the term "external" means out of the head. In another embodiment, one of the IMD and EPTD comprises a magnet and the other comprises a ferromagnetic material. In an embodiment the EPTD functions also as external pulse generator for supplying via the IMD electrical current to the nerves.

The charging device 106 is configured to charge an energy storage, such as one or more rechargeable batteries, comprised in the rechargeable instrument 104, such as in an EPTD. The charging device 106 is further configured and arranged to be portable—in other words, it can be carried. Optionally, the charging device 106 may be further configured and arranged to exchange data with the rechargeable instrument 104. The charging device 106 comprises two or more charging stations 110, each configured and arranged for receiving and retaining a rechargeable instrument 104—in this example, an EPTD 104. n the embodiment shown in FIG. 1, the charging device 106 comprises four charging stations 110. In the schematic depiction of FIG. 8, two charging stations 110 are shown.

The fourth component of the system is a mobile device 108. The mobile device 108 provides a user interface to monitor and set the parameters of the EPTD and IMD and to review the applied therapy. In FIG. 1 the mobile device 108 is a mobile phone. However, the mobile device can be any device providing a user interface and display enabling a user to control and monitor operating parameters of the EPTD and IMD, such as a tablet computer. Additionally or alternatively, the mobile device may provide a user interface and display enabling a user to control and monitor charging parameters of the EPTD and IMD.

Although the phrase "mobile phone" is used, this should be understood also comprising devices which provide a limited (or even no) traditional telephone functionality, such as voice calling, but provide one or means of communicating, such as with messaging apps. In general, "mobile phone" should be interpreted as a portable personal communications device.

In FIG. 1 and FIG. 8, the charging device 106 is comprised in a mobile device cover, more specifically a mobile phone cover. The mobile phone cover comprises a holder 120 for receiving and retaining the mobile phone 108.

A mobile phone cover may be made using one or more suitable materials, such as a fabric, a natural material, a plastic and/or a polymer. In the context of this disclosure, a cover for a mobile phone is typically configured and arranged to protect and/or conceal a portion of the external surface (or face) of the mobile phone 108, such as the screen side or the back. Mobile phone covers are also known which protect and/or conceal portions of more than one external surface (or face)—for example, a cover may conceal and/or protect both the screen and the back, as well as one or more sides.

Cases for a mobile phone are also known—traditionally a case is understood to enclose the mobile phone, but some covers also enclose the mobile phone. So, in the context of this disclosure case and cover should be considered as synonymous.

The holder 120 is configured and arranged to receive and retain the mobile phone 108. For example, using one or more magnets, one or more mechanical retainers, one or more protrusions, one or more recesses, one or more fasteners, one or more openings, one or more resilient elements, one or more elastic elements, one or more clamps, one or more hooks, one or more threaded elements, one or more pins, one or more adhesive elements, one or more coatings, and any combination thereof to retain the mobile phone 108.

Optionally, the mobile phone cover may be configured and arranged to receive and retail the holder 120, or the holder 120 may be rigidly attached to the mobile phone cover. Holder 120 should be interpreted as one or more elements cooperating to allow the mobile phone 108 to be received and retained in the mobile phone cover. The holder 120 may be configured and arranged to accept a wide range of mobile phones 108, or one or more specific types of mobile phone 108.

Each charging station 110 is configured and arranged to receive and retain a rechargeable instrument 104. For example, using one or more magnets, one or more mechanical retainers, one or more protrusions, one or more recesses, one or more fasteners, one or more openings, one or more resilient elements, one or more elastic elements, one or more clamps, one or more hooks, one or more threaded elements, one or more pins, one or more adhesive elements, one or more coatings, and any combination thereof to retain the rechargeable instrument 104.

In FIG. 1, each charging station 110 comprises a recess, configured to receive the rechargeable instrument 104. One or more magnets or mechanical retainers may be used, for example, to retain the rechargeable instrument 104. I Each charging station 110 is configured and arranged to allow the rechargeable instrument 104 to be removed, either directly by hand, or using a simple tool, a mechanically operated release and/or an electrically operated release. Preferably, each rechargeable instrument 104 can be removed manually—for example, an EPTD can be manually removed from a charging station by tilting and grabbing the EPTD, or by tilting the EPTD and gliding it out of a magnetic slot of the charging station 110.

In FIG. 1 and FIG. 8, the mobile phone 108 comprises an energy supply, and the portable charging device 106 is configured and arranged:

to transfer energy, in use, from the energy supply of the mobile phone 108, placed in the holder 120, to the two or more charging stations 110; and to transfer energy, in use, from the charging stations 110 to the energy storage of the rechargeable instrument 104 placed in the respective charging station 110.

The energy supply of the mobile phone 108 may comprise, for example, one or more rechargeable batteries.

By suitable configuration of the mobile phone cover and/or the portable charging device 106, different types of rechargeable instruments 104 may be accommodated. For example, one or more rechargeable instruments 104 may be an implantable device, an implantable neurostimulation device, an EPTD 104, a wearable device, a medical device, an implantable medical device (IMD) 102, a therapeutic device, a medical aid, a cosmetic device, a device for stimulating one or more nerves (neurostimulator), a device for stimulating one or more muscles, a device for stimulating one or more organs, a device for stimulating spinal cord tissue, a device configured for powering wirelessly a further device, a device configured for powering wirelessly a further rechargeable instrument 104, a personalized device, a custom-made device, a patient-specific device, a device for an individual, or any combination thereof. The rechargeable instrument 104 should not be construed as including one or more mobile phones 108.

Covers and cases are known for receiving a one or more bank/credit cards—however, such a card, even smartcards, should not be considered as a rechargeable instrument 104 in the context of this disclosure.

Although smartcards may have a degree of energy storage, used by smartcard readers to read data from the card, they do not operate as intended once they leave the region in which energy is being received. In the context of this disclosure, a rechargeable instrument 104 is configured and arranged to retain an amount of energy in its energy storage such that the instrument 104 can substantially operate as intended for a significant period of time when it is no longer receiving energy from the storage device 106.

In an alternative embodiment, the functionality of charging device 106 and mobile device 108 is combined in one apparatus. Furthermore, the charging device 106 may receive its energy from another source than the mobile device 108—for example, the charging device 106 may further comprise a charging energy storage, such as one or more rechargeable batteries. The charging device 106 may optionally be configured and arranged:

to transfer, in use, energy from the energy supply of the mobile phone 108, placed in the holder, to the charging energy storage; and to transfer, in use, energy from the charging energy to the two or more charging stations 110.

In an alternative embodiment of the charging device, a charging station 106 is configured to receive and charge more than one rechargeable instrument 104, such as more than one EPTD 104. In this embodiment, the EPTDs in the charging station are charged simultaneously.

Figure 5:
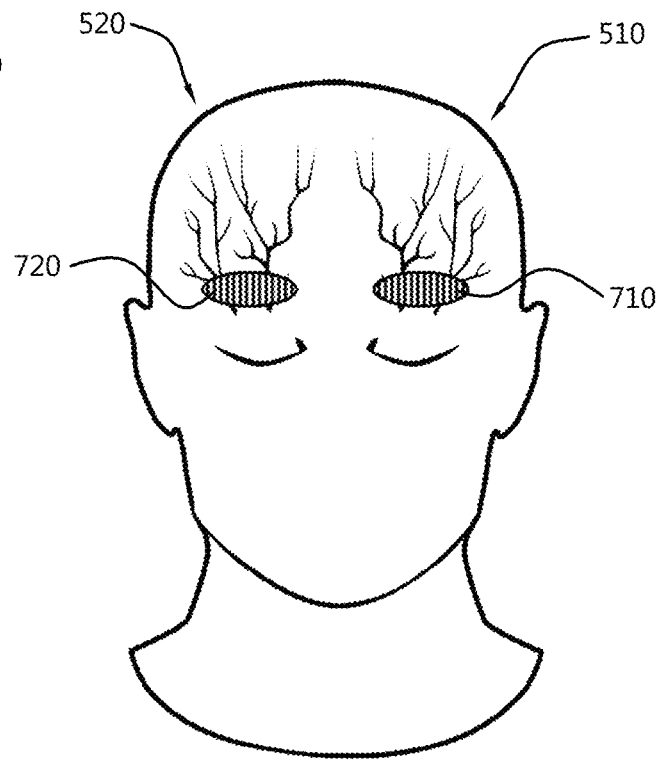
FIG. 5 and FIG. 6 show examples of nerves that may be stimulated using a suitably configured neurostimulation system.
Figure 6:
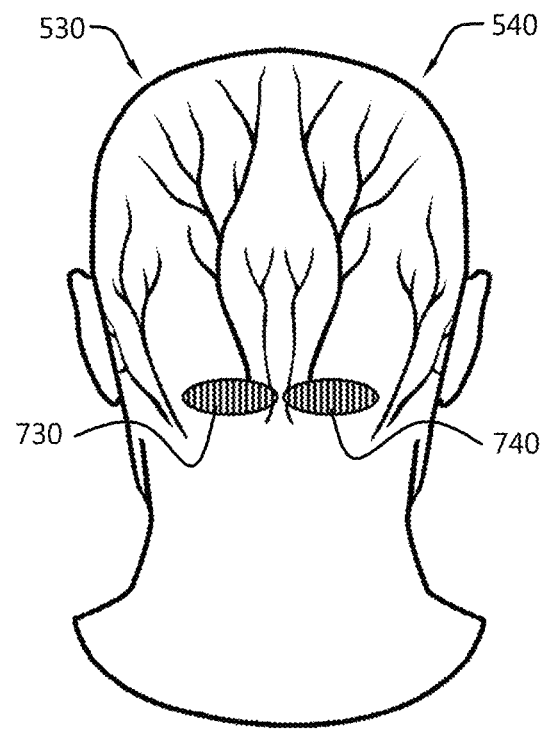

FIGS. 5 and 6 depict examples of nerves that may be stimulated using a suitably configured neurostimulation system 100 with an implantable distal end. It may provide neurostimulation to treat, for example, headaches or primary headaches.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured neurostimulation system 100.

Depending on the size of the region to be stimulated and the dimensions of the part of the device to be implanted, a suitable location is determined to provide the electrical stimulation required for the treatment. Approximate implant locations for the distal part of the stimulation device comprising stimulation devices 100 are depicted as regions:

location 810 for left supraorbital stimulation and location 820 for right supraorbital stimulation for treating chronic headache such as migraine and cluster.

location 830 for left occipital stimulation and location 840 for right occipital stimulation for treating chronic headache such as migraine, cluster, and occipital neuralgia.

In many cases, these will be the approximate locations 810, 820, 830, 840 for the implantable part of the neuro stimulation system 100.

For each implant location, 810, 820, 830, 840 a separate combinations of EPTD and IMD may be used. Where implant locations 810, 820, 830, 840 are close together, or even overlapping, a single stimulation system may be configured to stimulate at more than one implant location 810, 820, 830, 840. A plurality of stimulation devices 100 may be operated separately, simultaneously, sequentially or any combination thereof to provide the required treatment.

Figure 7:
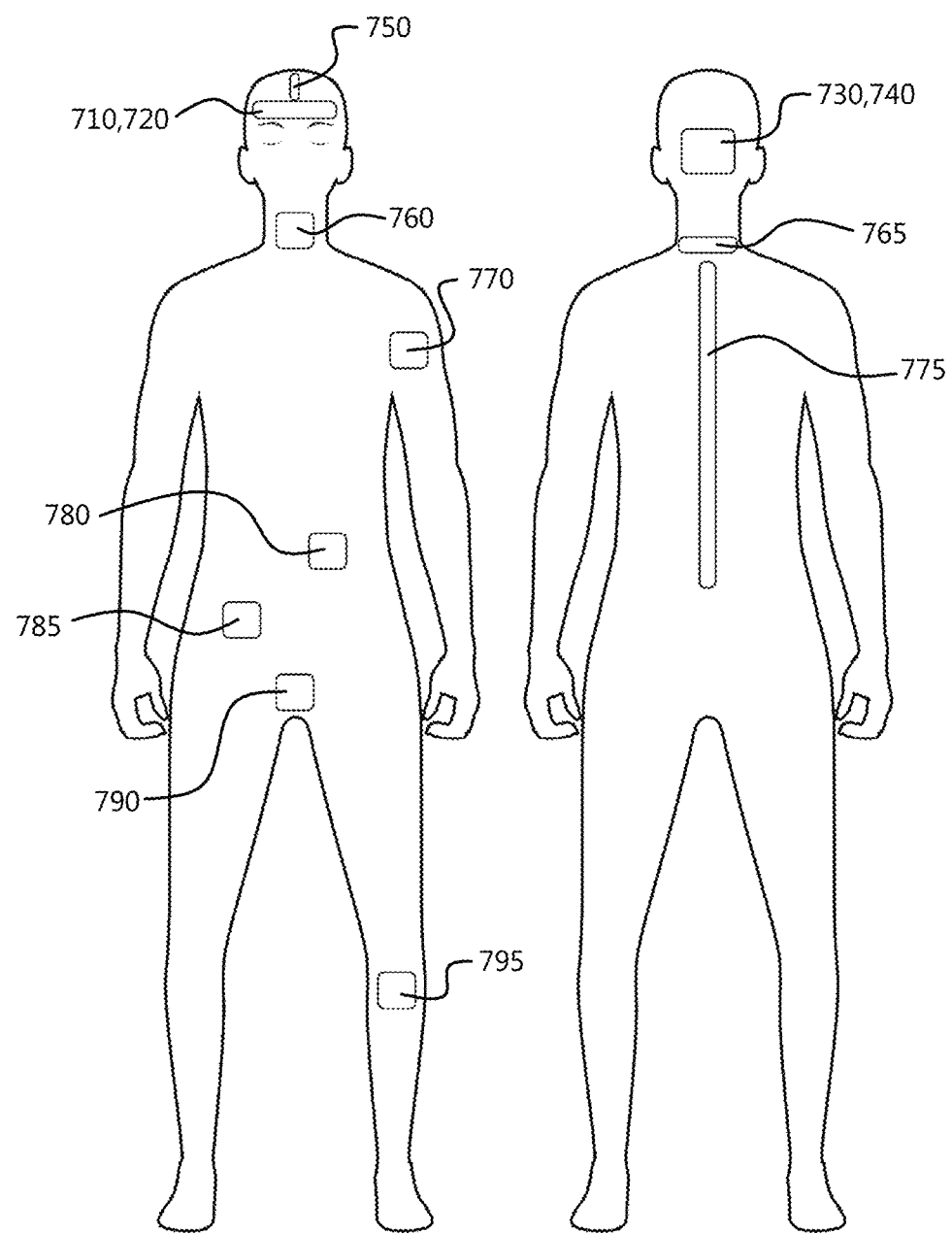
FIG. 7 shows further examples of nerves that may be stimulated using a suitably configured neurostimulation system.

FIG. 7 depicts further examples of nerves that may be stimulated using a suitably configured stimulation system 100 to provide neurostimulation to treat other conditions. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

location 810, 820 for cortical stimulation for treating epilepsy;

location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery location 860 for vagus nerve stimulation for treating epilepsy, depression, anxiety, bulimia, obesity, tinnitus, obsessive compulsive disorder, heart failure, Crohn's disease and rheumatoid arthritis;

location 860 for carotid artery or carotid sinus stimulation for treating hypertension;

location 860 for hypoglossal & phrenic nerve stimulation for treating sleep apnea;

location 865 for cerebral spinal cord stimulation for treating chronic neck pain;

location 870 for peripheral nerve stimulation for treating limb pain, migraines, extremity pain;

location 875 for spinal cord stimulation for treating chronic lower back pain, angina, asthma, pain in general;

location 880 for gastric stimulation for treatment of obesity, bulimia, interstitial cystitis;

location 885 for sacral & pudendal nerve stimulation for treatment of interstitial cystitis;

location 885 for sacral nerve stimulation for treatment of urinary incontinence, fecal incontinence;

location 890 for sacral neuromodulation for bladder control treatment; and location 895 for fibular nerve stimulation for treating gait or footdrop.

Other conditions that may be treated include gastroesophageal reflux disease, an autoimmune disorder, inflammatory bowel disease and inflammatory diseases.

IMD's 102 may be optimised for the stimulation of one or more nerves, one or more muscles, one or more organs, spinal cord tissue, brain tissue, one or more cortical surface regions, one or more sulci, and any combination thereof.

Figure 2:
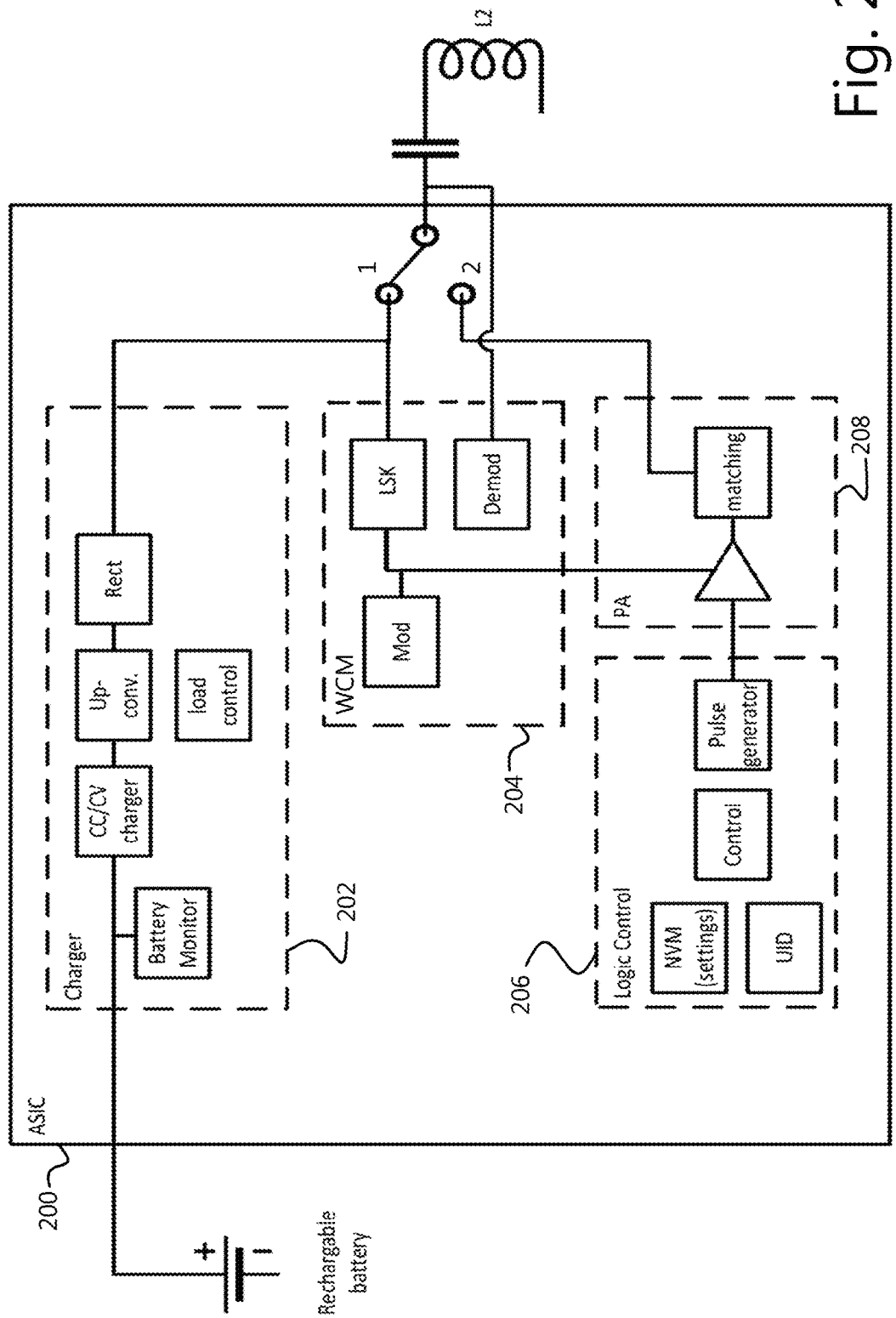
FIG. 2 shows a block diagram of the EPTD.

FIG. 2 shows a block diagram of an embodiment of an EPTD according to the present technology. The EPTD comprises an application specific IC (ASIC) 200, a rechargeable battery and a transmission/receiving coil L2 with or without a series-resonant capacitor. The ASIC comprises charger part 202, a Wireless Communication Module (WCM) part 204, a Logic control part 206 and a power amplifier (PA) part 208. The charger part 202 comprises commonly known circuitry such as a rectifier, an up-converter, charger circuitry having constant current (CC) and constant voltage (CV) mode, battery monitoring and load control. The rechargeable battery can be any type of suitable rechargeable battery. The WCM part 204 comprises commonly known circuitry for Wireless Communication via the coil L2, such as a demodulator, modulator and a load-shift keying (LSK) signal generator. The WCM part 204 enables the EPTD 104 to communicate with the IMD 102 and the charging device 106. The WCM part can be configured to apply any of the NFC standards, Qi interface standard or any other suitable proprietary wireless communication and energy transfer protocol. The Logic control part 206 comprises a pulse generator, control logic for controlling functions of the EPTD and a memory in which a number of IMD parameter sets are stored. An IMD parameter set comprises all control parameters an IMD needs to work properly and to apply a therapy. According to the present technology, each IMD parameter set comprises a unique identification code having a value linked to the unique identification code of an IMD 102. In this way, the EPTD 104 knows which IMD parameter set has to be used for which IMD. The ASIC further comprises a power amplifier PA block comprising an amplifier and a matching circuit. A selector is used to switch between charging mode and IMD powering mode. In charging mode, the internal battery of the EPTD is charged. In IMD powering mode, power is transmitted to an IMD. In both modes, data transfer is possible. The EPTD is configured to send, preferably at regular intervals, a power signal to the IMD. The energy transferred in a power signal should be sufficient to enable the IMD to generate a stimulation pulse and to power the electronic circuitry of the IMD up to at least the next power signal. In an embodiment the power signal is a pulse-like signal. The EPTD can be configured to send a continuous power signal to the IMD. However, this has the disadvantage that unnecessary power is consumed by the IMD in the human body, which can cause heating of the tissue around the IMD.

Figure 3:
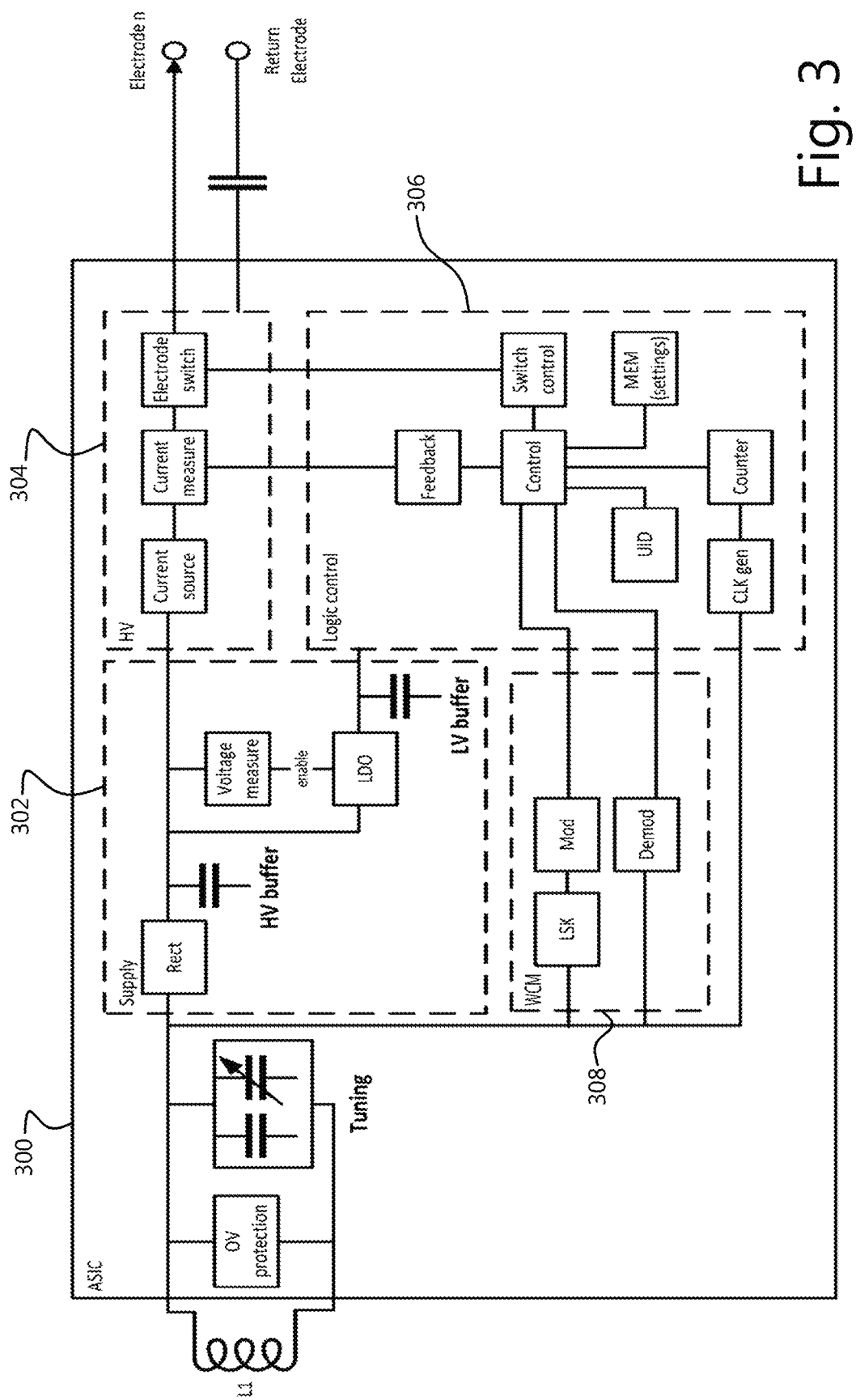
FIG. 3 shows a block diagram of the IMD.

FIG. 3 shows an example of block diagram of the IMD according to the present technology. This block diagram is not specific for the invention, other block diagrams can be devised. The IMD comprises an ASIC 300, a transmission/receiving coil L1 and one or more Electrodes (not shown). The ASIC 300 comprises an Overvoltage protection circuitry, tuning circuitry, a supply part 302, a high voltage (HV) part 304, a logic control part 306 and an NFC part 308.

The supply part 302 comprises a rectifier, a HV buffer in the form of a capacitor, voltage measuring unit measuring the voltage of the HV buffer and controlling a Low-DropOut regulator and a low voltage buffer in the form of another capacitor. The Low-DropOut regulator supplies energy to the low voltage buffer. The capacity of the low voltage buffer is sufficient to power the logic control part 306 and NFC part 308 to at least the next power signal. The high voltage part 304 is configured to supply a stimulation pulse to the electrodes of the IMD. To perform this function, the high voltage part 304 comprises a current source, a current measuring unit and an electrode switch. The measured current is supplied to the logic control part 306. The electrode switch is controlled by a switch control signal generated by the logic control unit 306. The electrode switch enables to limit the amount of current of the stimulation pulse supplied to the electrodes.

The logic control part 306 comprises a memory to store the IMD parameter set, a unique identification code permanently stored in a memory location, a clock generator for generating a clock signal for the logic control unit, a counter for counting the number of clock cycles, a switch control signal generator a feedback circuit and a controller. The clock generator derives a clock signal from the RF frequency. As a result the clock signal of the EPTD and IMD will have the same clock frequency. The feedback circuit measures the current to the electrode(s) and determines a feedback signal to the EPTD to enable to EPTD to control the level of the power signal generated by the EPTD. In an embodiment to reduce the dimensions of the ASIC the memory to store the IMD parameter set is a volatile memory, along with a compact non-volatile memory to store the IMD identification code (e.g. using fuses). In another embodiment, at least a part of the IMD parameter set is stored in non-volatile memory.

The WCM part 308 comprises commonly known circuitry for Wireless Communication via the coil L1, such as a demodulator, modulator and a load-shift keying (LSK) signal generator. The WCM part 308 enables the IMD to communicate with the EPTD.

In general, the portable charging device further comprises a charging circuit, the charging circuit comprising one or more electrical components, configured and arranged to control charging in use. Optionally, one or more of these components may comprise one or more coils, configured and arranged to transmit and/or receive energy wirelessly.

Figure 4:
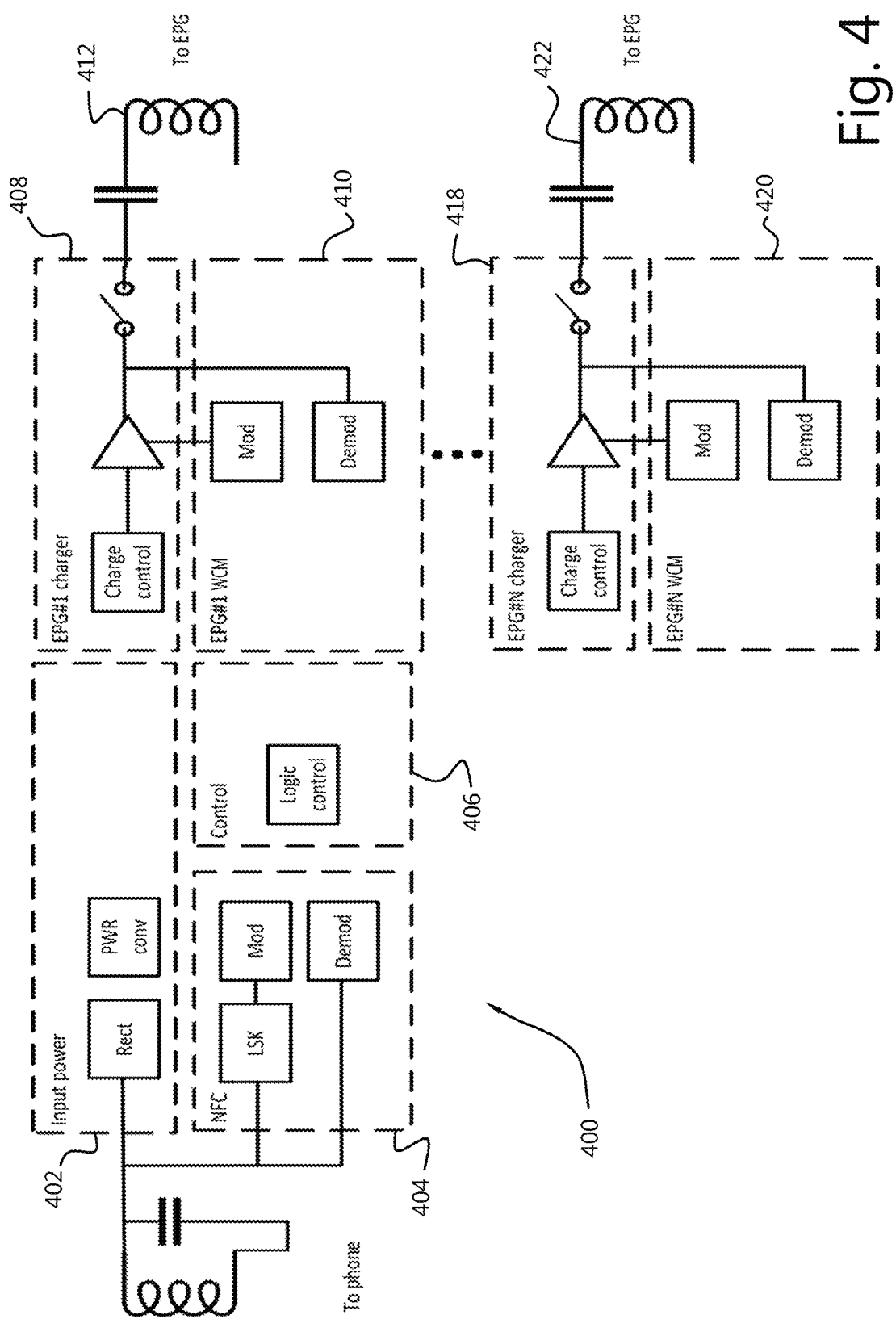
FIG. 4 shows a block diagram of a charging circuit.

FIG. 4 shows a block diagram of a first embodiment of a charging circuit 400, comprised in the portable charging device 106. FIG. 8 schematically depicts the main interfaces of the charging circuit 400 with the other components of the portable charging device 106.

The charging circuit 400 comprises a coil, connected to an input power part 402, to wirelessly receive power from a mobile phone 108 by means of a suitable energy transfer protocol. For example, Qi, Powermat, Rezence, WiPower, Open Dots, PMA, Wireless Power Transfer (WPT), Simultaneous Wireless Information and Power Transfer (SWIPT), inductive coupling, resonant inductive coupling, capacitive coupling, and any combination thereof. The mobile device 108 comprises a corresponding coil 125, configured and arranged to transfer energy to the input power part 402.

Configuring and arranging one or more coils to transmit and/or receive energy wirelessly may require optimising one or more mechanical, electrical and/or magnetic parameters relevant for energy transfer. For example:
current, voltage, energy charge and/or power supplied to the transmission coil;
frequency, waveform shape, repetition rate, operation duration of the transmission energy;
relative proximity, alignment and/or orientations of the transmitting and receiving coils;
relative dimensions of the transmitting and receiving coils;
the number of turns, the conductor materials used, the conductor thickness;
materials comprised in the cover, and in particular, in the charging station to increase energy transfer.

Optionally, the coil may be further configured and arranged to exchange data with the mobile phone 108 by means of a suitable wireless communication protocol, or a further coil may be so configured. For example, Bluetooth, Bluetooth LE, NFC, Low-power WAN, LTE, Qi, Wi-Fi, and any combination thereof. The coil 125 may be further configured and arranged to exchange data with the coil of the input power part 402, or a further coil may be so configured.

Some protocols may allow both energy transfer and wireless communication to a suitable degree.

The charging circuit 400 further comprises the input power part 402, and at least one charging station 110. If optionally data is to be shared, the charging circuit 400 further comprises a WCM part 404.

The charging circuit 400 associated with a charging station 100 comprises a charger part 408, 418, and a coil 412, 422 configured and arranged for energy transfer. If optionally data is to be shared, the charging station part of the circuit 400 further comprises a WCM part 410, 420 and either a suitably configured coil 412, 422 or a further coil optimised for data communication.

A charging station 110 is configured to wirelessly transfer energy to the energy storage of the rechargeable instrument 104 placed in the respective charging station, for example to charge the rechargeable battery of an EPTD placed in the charging station. Optionally, data may be exchanged with the EPTD by means of the WCM part 404. The WCM part 404 of the charging circuit 400 comprises commonly known circuitry of a demodulator, a modulator and a load-shift keying (LSK) signal generator.

The rechargeable element 104 further comprises a corresponding coil 115, configured and arranged to receive energy from the energy transfer coils 412, 422 of the charging circuit 400.

In summary, the portable charging device 106 is configured and arranged:
  to wirelessly transfer energy, in use, from the energy supply of the mobile phone 108, placed in the holder, to the charging circuit 400;
  to transfer energy through the charging circuit 400 (wired), in a predetermined and/or controlled manner, to two or more charging stations 110; and
  to wirelessly transfer energy, in use, from the charging stations 110 to the energy storage of the rechargeable instrument 104 placed in the respective charging station 110.

Optionally, the portable charging device 106 may be further configured and arranged, in use:
  to transfer data from the mobile phone 108 to one or more rechargeable instrument 104;
  to receive data by the one or more rechargeable instrument 104 from the mobile phone 108;
  to transfer data from one or more rechargeable instrument 104 to the mobile phone 108;
  to receive data by the mobile phone 108 from the one or more rechargeable instrument 104;
  to transfer data from a first rechargeable instrument 104 to a further rechargeable instrument 104;
  to receive data by a further rechargeable instrument 104 from the one or more rechargeable instrument 104); and any combination thereof.

Optionally, the charging device 106 and the charging circuit 400, may be configured and arranged to allow a degree of energy transfer between rechargeable instruments 104.

For example, if one or more rechargeable instruments 104 comprise a further energy supply, the portable charging device 106 may be further configured and arranged:

to wirelessly transfer energy, in use, from the further energy supply of the one or more rechargeable instruments 104 placed in a first charging station 110 to the charging circuit 400;
  to transfer energy through the charging circuit 400 (wired), in a predetermined and/or controlled manner, to one or more further charging stations 110; and
  to wirelessly transfer energy, in use, from the one or more further charging stations 110 to the energy storage of the rechargeable instrument 104 placed in the respective further charging station 110.

Where required, the charging device 400 may be configured and arranged to control the charging in a predetermined and/or controlled manner.

According to an embodiment of the present technology, the IMD parameter set of an IMD is stored in volatile memory. As a result, the content of the IMD parameter set in the IMD is lost as soon as the low voltage buffer of the IMD is out of charge. The IMD is powered wirelessly by the EPTD. The EPTD generates at regular intervals a power signal to power the IMD. Depending on the implementation, during and/or after the generation of a power signal, the IMD and EPTD can exchange data. So when an EPTD is disconnected from an IMD, the IMD will be out of power very quickly as it does not receive power signals anymore. Consequently the IMD will lose any data stored in volatile memory and thus the IMD parameter set which is necessary to apply the correct treatment. To ensure that the treatment of headaches is not interrupted too long, the user must have at least two EPTDs. This allows the user to have always an EPTD with a fully charged rechargeable battery available for replacing an EPTD with an empty rechargeable battery. However if the user has two IMD for treatment of chronic headache, the EPTD could be combined with any of the two IMDs. However each IMD could have its own IMD parameter set defining the treatment to be applied. So to enable an EPTD to supply an IMD parameter set to any the EPTD in the medical system, the EPTD must have the IMD parameter set of at least all IMDs used in the system. Furthermore, the EPTD should not send to an IMD a parameter set that has to be used by another IMD. To ensure this, each IMD has its own unique IMD identification code permanently stored in an addressable location. Furthermore, in the EPTD, the IMD parameter set comprises an associated unique identification code. The unique identification code can be integral part of the IMD parameter set. It might also be possible that the EPTD stores in its memory a linkage between an IMD parameter set and a unique IMD identification code.

When an EPTD is magnetically coupled to an IMD, the EPTD will transmit a power signal to the IMD. The power signal will awake the IMD. After the IMD is activated, the IMD will be in not-connected mode. In not-connected mode, the IMD will transmit its unique identification code to the EPTD after the IMD is sufficiently powered by the power signal. The EPTD will receive the unique identification code and subsequently search in its memory for an IMD parameter set having an associated unique identification code which matches the unique identification code received from the IMD. If there is a matching identification code, the EPTD will transmit the associated IMD parameter set to the IMD together with the associated unique identification code. The IMD verifies whether the associated unique identification code corresponds to its own unique identification code. If there is a match, the IMD will switch to connected mode. If there is not a match, the IMD stays in non-connected mode. As a result, the IMD will retransmit to the EPTD its unique identification code after the receiving a subsequent power signal. In connected mode, the IMD could regularly transmit its current parameter set to EPTD. In this way, also adjustment of the IMD parameter set by the IMD is regularly updated in the corresponding IMD parameter set stored in the memory of the EPTD. In this way, the EPTD stores an actual IMD parameter set in its memory.

In the portable charging device 106, the following method is applied. When an EPTD is positioned in a charging station 110 of the charging device 106, the charging device 106 will request to transmit at least the IMD parameter set that has been transmitted to an IMD after the last recharging action of said IMD. This IMD parameter set may have parameter values that have been modified by the IMD during the period that the EPTD had powered the IMD. In an embodiment, the IMD parameter set comprises a time stamp indicating the time when the latest modification was made or the time when the EPTD most recently received the IMD parameter set from the IMD.

Optionally, the portable charging device 106 may further comprise one or more memory components, configured and arranged to store and/or distribute one or more parameter sets of data. Optionally, one or more memory components may be comprised in the charging circuit 400.

After receipt of an IMD parameter set from the EPTD, the charging device 106 may update the IMD parameter set in its own parameter set memory. The updating may depend on the time stamp of the IMD parameter set. In an embodiment, an IMD parameter set is only replaced by a new IMD parameter set when the time stamp of the new parameter set from the IMD is later in time than the time stamp of the parameter set currently stored in a parameter set memory of the charging device 106. It should be noted that each parameter set stored in the parameter set memory of the charging device has a corresponding unique IMD identification code.

After the charging device 106 has received a new IMD parameter set, the charging device 106 distributes the parameter set to all EPTDs that are (or will be) located in the other charging stations. In this way, all EPTDs will have the same IMD parameter sets stored in its memory. In an alternative embodiment, the charging device 106 distributes all parameter sets stored in its parameter set memory to all EPTDs located in the charging stations 110. In this alternative embodiment, all EPTDs located in the charging device 106 will have the same IMD parameter sets for all IMD used in the medical system. Thus when an EPTD is placed in a charging station 110 of the charging device 106, the charging device 106 first obtains at least the IMD parameter sets from the EPTD which content has been changed after its last removal from the charging device 106. Subsequently, the charging device 106 transmits all the IMD parameter sets stored in its parameter set memory to the last placed EPTD in the charging stations 110 to update the IMD parameter sets in the EPTD. Furthermore, the charging device 106 transmits at least the IMD parameter sets that have been updated after obtaining the IMD parameters from the EPTD after placement in a charging station 110 to the EPTDs located in the other charging stations. Thus it might be possible that when an EPTD that has not been used for a long time is placed in the charging device 106, the changed IMD parameters sets that are submitted to the charging device 106 are not used to update the corresponding IMD parameter sets stored in the parameter set memory of the charging device 106. This is due to the fact that the time stamps associated with the IMD parameters sets from the EPTD indicate a moment in time which is before the moment in time indicated by the time stamps associated with corresponding IMD parameter sets having the same unique identification code and stored in the parameter set memory of the charging device 106. Consequently, the charging device 106 will only update the IMD parameter sets in the EPTD that has not been used for a long time.

As described above, the EPTD generates a pulse shaped power signal. In an embodiment, the IMD controls which part of the pulse shaped power signal is passed to the electrodes of the IMD to form the stimulation pulse. So the EPTD determines when a stimulation pulse could be supplied to the electrodes and the IMD controls the beginning and end of the stimulation pulse. In an alternative embodiment, the IMD comprises a pulse generation module and pulse energy storage with a capacity that is sufficient for the IMD to generate a burst of stimulation pulses with a duration sufficient to apply a therapy according to the IMD parameter set. To be sure that the EPTD and IMD uses the same IMD parameter sets to generate the stimulation pulse, the EPTD sends every now and then a command to the IMD comprising a unique identification code associated with the IMD parameter set which the EPTD is using to generate the power signals. If the unique IMD identification code in the command transferred from the EPTD to the IMD differs from the unique IMD identification code of the IMD parameter set which the IMD currently is using to form the stimulation signal, the IMD will detect this and it will change to the status of the IMD from connected mode to not-connected mode. In this way, the risk that incorrect stimulation pulses will be supplied to the electrodes is reduced significantly. For the same reason in an embodiment, the IMD is configured in connected mode to transmit intermittently its unique IMD identification code to the EPTD. The EPTD will check whether said unique IMD identification code matches with the IMD identification code of the IMD parameter set that the EPTD uses to generate the power signals at regular intervals. In an embodiment, after detection of a mismatch, the EPTD stops with the generation of subsequent power signals for a predetermined time to force the IMD to run out of charge such that the IMD content of its memory is cleared and the IMD begins to transmit its IMD identification code to the EPTD. After receipt of the IMD identification code by the EPTD, the EPTD will transmit the IMD parameter set associated with the same IMD parameter code to the IMD. As a result the EPTD and IMD use the parameter sets having the same IMD identification code.

As described before, the memory of the IMD can be a volatile memory. Furthermore, there might be periods in time wherein no stimulation pulses are supplied to the electrodes of the IMD and/or no communication between the EPTD and IMD has to take place in the time period between two power signals. For that case, the IMD has an ultra-low power mode. In ultra-low power mode of the IMD, only the clock generator generates a clock signal to keep the IMD alive to the next power signal. The energy storage in the capacitor to power the electronics is chosen such that the IMD stays alive up to at least the next power signal. In an embodiment, the period of time to stay alive in low power mode is a device specific parameter permanently stored in the IMD. This parameter is submitted to the EPTD to define at the EPTD the period of time between two charging pulses. Furthermore, IMD could transmit a parameter to the EPTD which is indicative for the energy storage capacity of the capacitor for powering the electronics of the IMD. This parameter is used to limit the energy of a power signal in case no stimulation pulse has to be supplied to the electrode(s) of the IMD. In other words, the IMD is configured to operate at least in a first operating mode (ultra-low power)

and a second operating mode (normal operation). The EPTD is configured to determine the operating mode of the IMD, and to generate power signals with a time interval between two power signals depending on the determined operating mode of the IMD. The IMD further comprises an energy storage with an energy storage capacity that enables the IMD to hold the data stored in the volatile memory for more than one time interval and preferably not more than two time intervals, wherein the time interval is defined by the operating mode determined by the EPTD and parameters related to the energy storage capacity and energy consumption of the electronics of the IMD in the respective modes. It should be noted that said parameters can be stored in the IMD parameter set as each IMD comprises its own parameter set which is linked to the unique IMD identification code.

So, If the period of no communication/no stimulation lasts longer than the energy stored in the capacitor allows in ultra-low power mode, a short power signal with low amplitude can be given to recharge the capacitor instead of a power signal that is also suitable to supply a stimulation pulse to the electrodes. The later power signal has a high amplitude for a longer time.

In another embodiment, the IMD is configured to communicate with the EPTD about the energy stored in the capacitor for powering the electronics of the IMD and optionally the pulse energy storage for generating of the stimulation pulses internally by the IMD. This embodiment enables the IMD to control the characteristics of the power signal generated by the EPTD, such as but not limited to: amplitude, pulse width and length of the power signal.

In an embodiment, the EPTD generates a continuous power signal. In this embodiment, the IMD will transmit in not-connected mode at regular intervals it unique IMD identification code. After receiving an IMD parameter set including said unique IMD identification code, the IMD switches to connected mode.

In an alternative embodiment, the EPTD transmits wirelessly all IMD parameter sets stored in its memory when the EPTD detects that an IMD receives power from the EPTD. In this embodiment, the IMD receives all IMD parameter sets transmitted by the EPTD. The IMD retrieves from each IMD parameter set the unique identification code included in said IMD parameter set. When the retrieved unique identification code matches its own unique IMD identification code, the IMD deploys said parameter set to enable the IMD to provide the electrical stimulation defined by the IMD parameter set to the body where the IMD is implanted.

In an embodiment, the charging device 106 and/or comprises a user interface to adapt the IMD parameter sets. If there is no user interface on the EPTD, the charging device 106 may also pass on adapted parameter sets to the EPTD, and the charging device 106 may make adjustments based on user feedback (e.g. a smartphone user interface where the patient indicates how effective a therapy has been) or based on usage information (how long did the user actually use the EPTD). The usage information can also be read by the charging device 106 from the EPTD).

In the embodiments described above, the IMD is a neuro stimulation device. The presented technology can also be used in implants for other applications that control electronically for example micro valves or pumps implanted in a body.

In many applications where rechargeable instruments 104 are used, common problems including the user forgetting to recharge the instruments 104 and/or the user having too little time to fully recharge the instruments 104.

Especially where the rechargeable instruments 104 are used for a personalized application, such as a personalised therapy, stimulation or medical use, users become more reliant and dependent on the correct operation of these instruments, resulting in a severe inconvenience if they are not sufficiently charged. In this context, personalized means that the instruments 104 are optimised for a few users—in other words, in case of a defective personalized rechargeable instrument 104, the user has very few possibilities to find a replacement. The personalized rechargeable instruments 104 are unlikely to be available for immediate use as mass-produced devices, commodity devices, or off-the-shelf items.

The degree of personalization is greatly increasing, which makes the inconvenience worse. In some cases, where the rechargeable instruments 104 are custom-made, patient-specific or patient-adaptable, the rechargeable instruments 104 should only be used by one user or an individual—if used by others, the rechargeable instruments 104 may just operate incorrectly. However, in some critical cases, the use by others may even pose a substantial health risk.

In systems where critical functionality is divided over two or more devices, and one of these is a rechargeable instrument 104 for powering (either wired and/or wirelessly) a further device (for example, an EPTD 104 and IMD 102), the degree of inconvenience is similar as these two or more devices must be paired to a high degree. Dividing the functionality over a plurality of devices may increase the chance that one of these devices is not operable or even forgotten as there are more devices to keep track of. In addition, dividing the function may result in smaller devices, which are even more likely to be lost.

Custom-made means that it is intended to address a specific anatomo-physiological features or pathological condition of the individual (or user) for whom it is intended. Patient-specific means that it is produced based on a standard device template model, or specified design envelope (e.g., minimum and maximum dimensions, performance limits, and other clinically relevant factors), that is matched to a patient's anatomy using techniques such as scaling of the device based on anatomic references, or by using the full anatomic features from patient imaging. Patient-adaptable means that it is a mass-produced medical device that must be adapted or assembled at the point of care, in accordance with the manufacturer's instructions, to suit an individual's specific anatomo-physiologic features prior to use. Mass-produced means identical devices that are produced in continuous production runs or homogenous batches.

By providing a portable charging device 106 in a mobile phone cover there is a reduced risk that an instrument will not work properly when the user wishes to use it. In addition, there may also be lower chance that the user will forget to take the rechargeable instruments with them when they are travelling and/or away from home. Most users will reliably charge their phone 108, and are used to taking it with them when they are travelling and/or away from home.

Additionally, many mobile phones 108 are dimensioned to be portable, particularly commercially available mobile phones 108.

Preferred dimensions for the mobile phone cover are those suitable for transport in a small bag, and most preferably pocket-sized.

Smaller dimensions should preferably be used, as this may increase portability and may increase the likelihood that the user will use the cover regularly, preferably every day.

Figure 11:
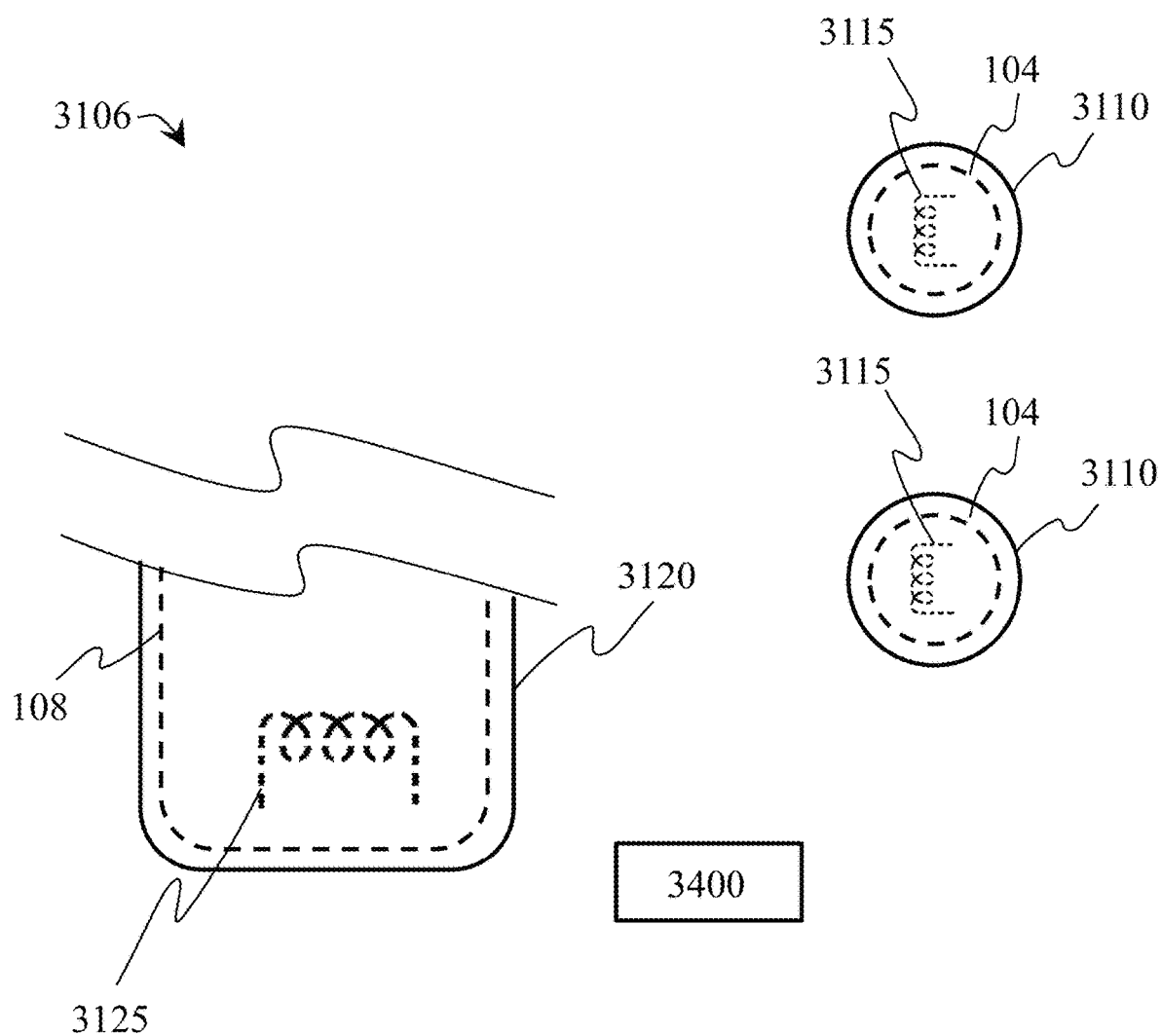

FIG. 11 depicts schematically a further embodiment of a charging circuit 3400 comprised in a further embodiment of a charging device 3106.

The charging device 3106 is the same as that depicted in FIG. 8, except for:
- the charging circuit 3400 does not comprise one or more coils to receive energy from the mobile phone 108;
- the charging circuit 3400 does not comprise one or more coils to transfer energy to the two or more charging stations 3110; and
- the charging circuit 3400 does not transfer charging energy through itself (wired) from the mobile phone 108 to the two or more charging stations 3110.

In other words, the portable charging device 3106 is configured and arranged:
- to wirelessly transfer energy, in use, from the energy supply of the mobile phone 108, placed in the holder, to the energy storage of the rechargeable instruments 104 placed in the charging stations 3110.

Where required, the charging device 3400 may be configured and arranged to control the charging in a predetermined and/or controlled manner.

By suitable configuration and arrangement of the energy transfer coil 3125 comprised in the mobile phone 108, the holder 3125 of the mobile phone 108, the two or more charging stations 3110, and the energy reception coils 3115 comprised in the one or more rechargeable instruments 104, a charging circuit 3400 may be made optional. Additionally or alternatively, the control of the charging in a predetermined and/or controlled manner may be performed using a software app, running on the mobile phone 108.

Figure 10:
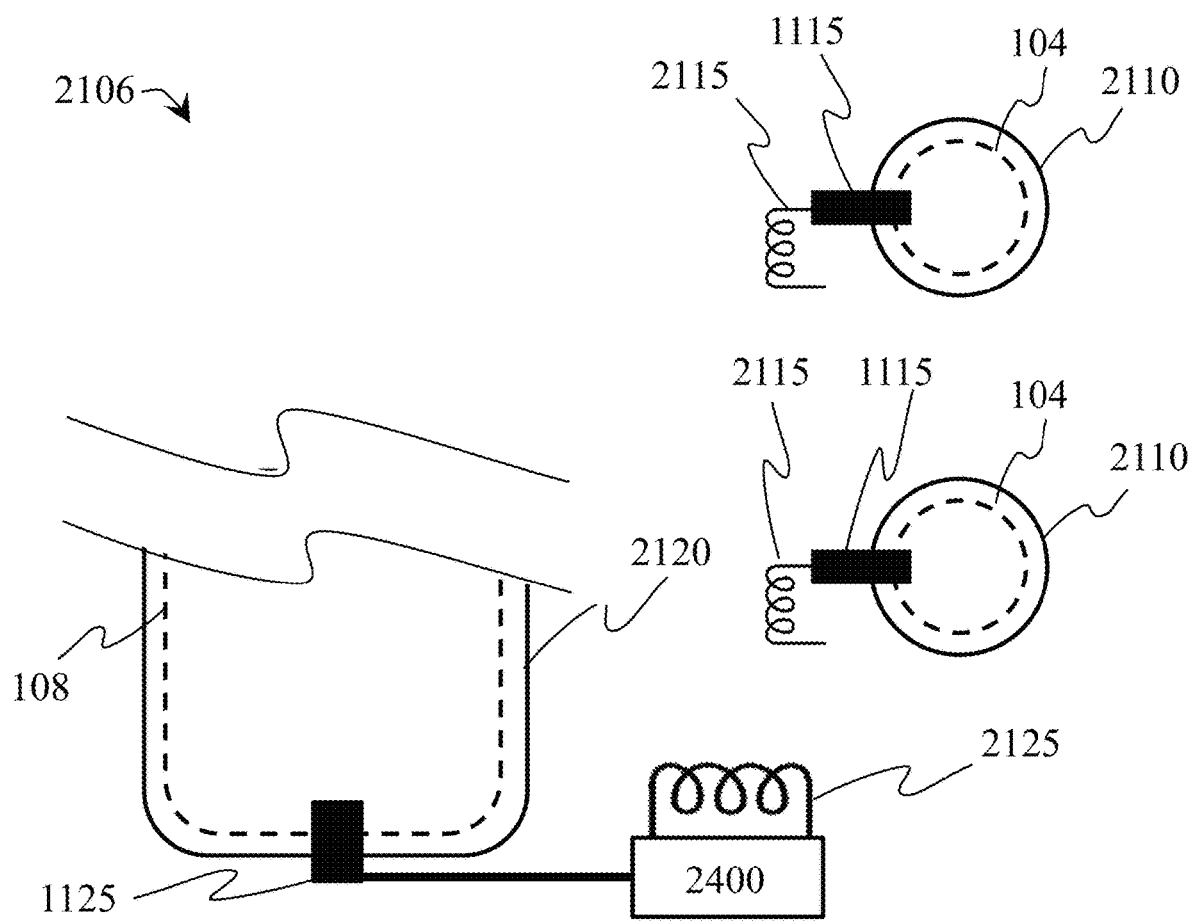

FIG. 10 depicts schematically another embodiment of a charging circuit 2400 comprised in a further embodiment of a charging device 2106.

The charging device 2106 is the same as that depicted in FIG. 11, except for:
- the charging circuit 2400 comprises one or more electrical interconnections and/or electrical connectors 1125, configured and arranged to connect to the mobile phone 108 when placed in the holder 2120, and further configured and arranged to transfer energy wired from the energy supply of the mobile phone 108 to the charging circuit 2400;
- the charging circuit 2400 comprises a coil 2125 to transfer energy wirelessly from the charging circuit 2400 to the two or more charging stations 2110; and
- the two or more charging stations 2110 comprises a coil 2115 and one or more electrical interconnections and/or electrical connectors 1115 to receive energy wirelessly from the charging circuit 2400, and to transfer energy wired to the respective rechargeable instrument 104.

In this embodiment 2106, it is not necessary that the mobile device 108 comprises an energy transfer coil as the energy is transferred using the coil 2125 comprised in the charging circuit 2400. However, it may be advantageous to use a mobile device with an energy transfer coil, and to transfer energy at substantially the same time that energy is transferred by the energy transfer coil 2125 of the charging circuit 2400.

Similarly, it is not necessary that the rechargeable instruments 104 comprise an energy receiving coil as the energy is transferred using the energy receiving coil 2115 and the interconnections and/or connectors 1115 (also called galvanic contacts) comprised in the charging station 2110.

Where required, the charging device 2400 may be configured and arranged to control the charging in a predetermined and/or controlled manner.

Figure 9:
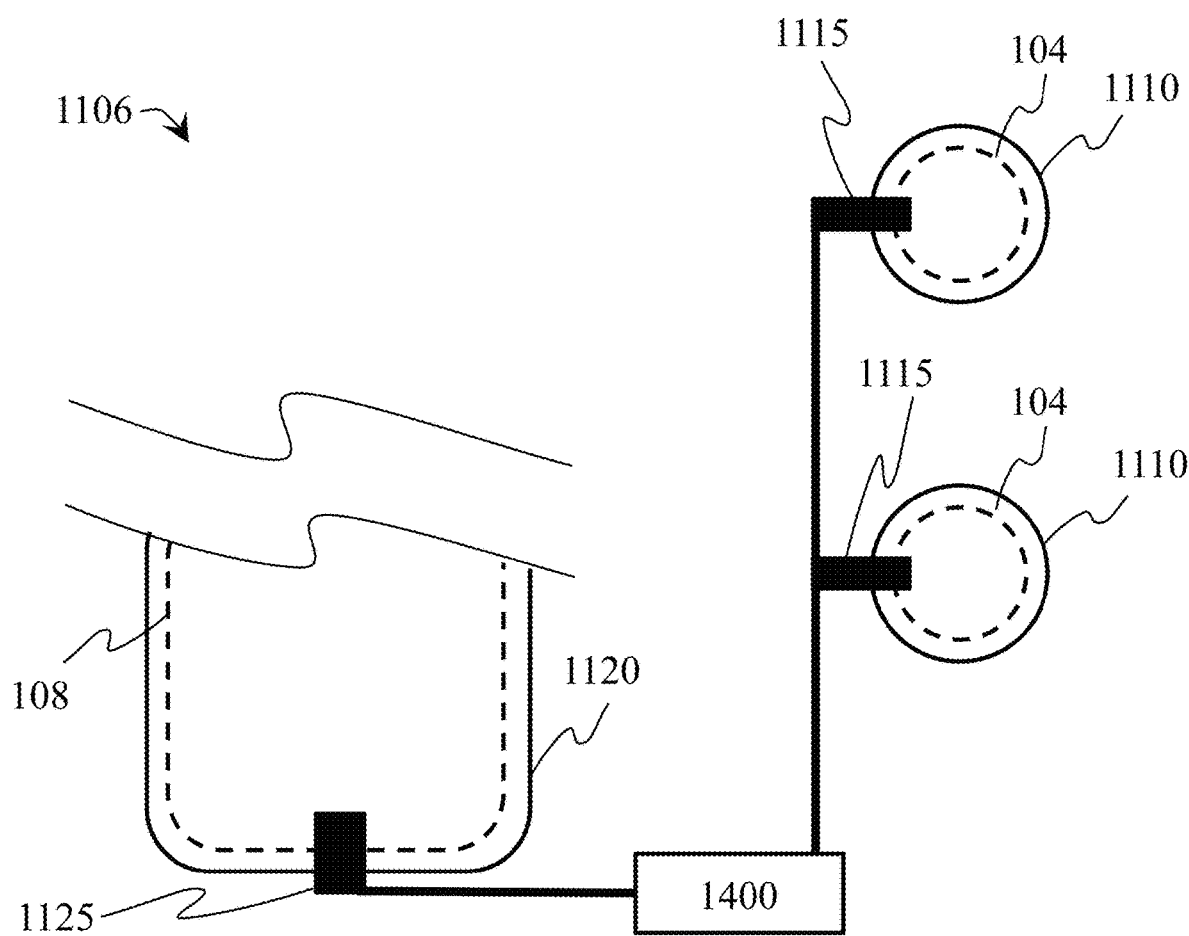
FIG. 9, FIG. 10 and FIG. 11 schematically depict further charging circuits comprised in a charging device.

FIG. 9 depicts schematically yet another embodiment of a charging circuit 1400 comprised in yet a further embodiment of a charging device 1106.

The charging device 1106 is the same as that depicted in FIG. 10, except for:
- the charging circuit 1400 comprises further electrical interconnections and/or electrical connectors 1115, configured and arranged to connect to the mobile phone 108 when placed in the holder 1120, and further configured and arranged to transfer energy wired from the energy supply of the mobile phone 108 to the charging circuit 1400; and
- the charging circuit 1400 comprises further electrical interconnections and/or electrical connectors 1115, configured and arranged to connect to the two or more rechargeable instruments 102 when placed in the charging stations 1110 to transfer energy wired from the charging circuit 1400.

In this embodiment 1106, it is not necessary that the mobile device 108 comprises an energy transfer coil as the energy is transferred using the interconnections and/or connectors 1115 comprised in the charging circuit 1400. Similarly, it is not necessary that the rechargeable instruments 104 comprise an energy receiving coil as the energy is transferred using the interconnections and/or connectors 1115 comprised in the charging circuit 1400.

Where required, the charging device 1400 may be configured and arranged to control the charging in a predetermined and/or controlled manner.

A further problem with rechargeable instruments 104, and in particular, personalized rechargeable instruments, is the desire by a user for discretion. A user or individual may wish to transport and charge the instruments 104 without revealing their presence to others. In particular, when the rechargeable instruments 104 are configured for one or more therapeutic, stimulation and/or medical uses, the user may not wish others to be aware that they have a condition which requires treatment.

The mobile phone cover as disclosed herein may be modified to provide inconspicuous and unobtrusive storage and charging. FIG. 1 depicts a mobile phone cover in perspective view, and FIG. 12 depicts a portion of the same mobile phone cover schematically after the mobile phone 108 has been placed in the holder 120.

Figure 12:
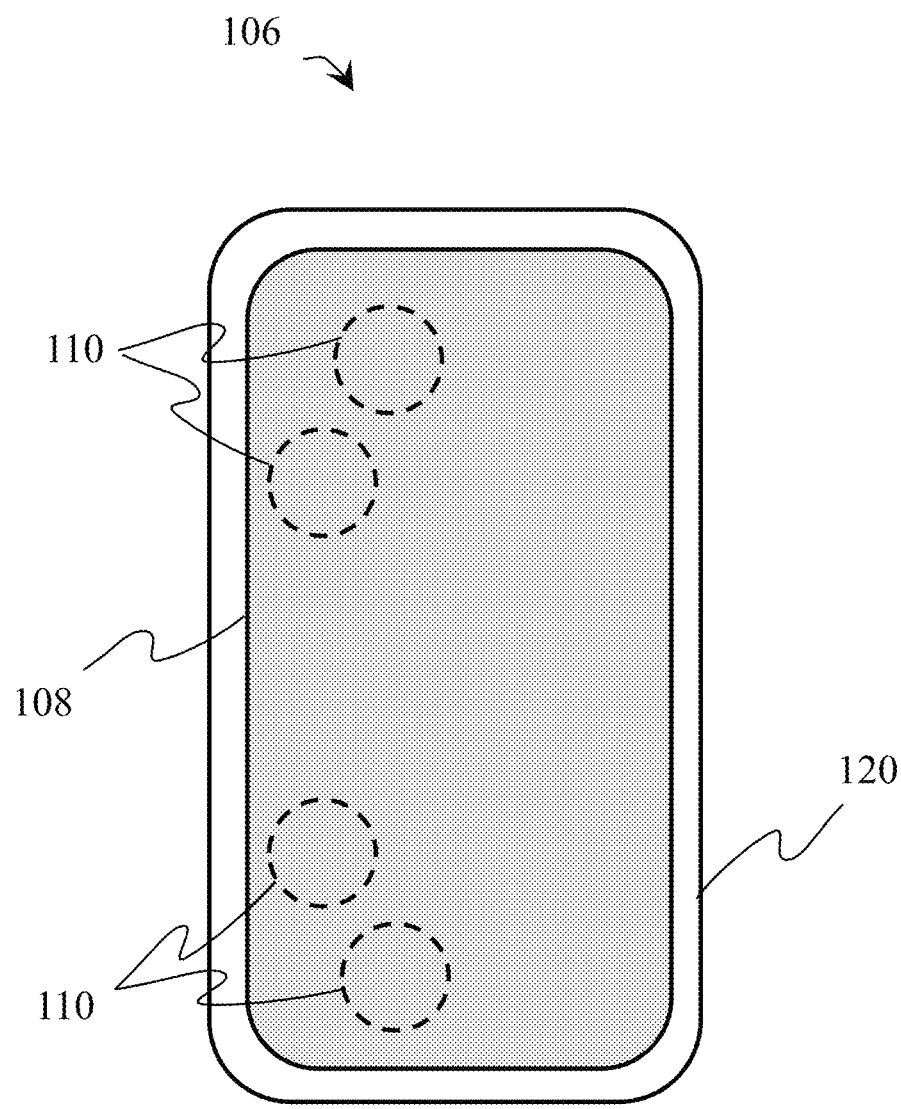
FIG. 12 depicts schematically a mobile phone cover with discreet storage of one or more rechargeable instruments.

FIG. 12 shows the holder 120 portion of the mobile phone cover as viewed from directly above the screen size or the back size of the mobile phone 108. Preferred is the mobile phone cover is configured and arranged such a user may view at least a portion of the mobile phone 108 display when the mobile phone 108 is retained in the mobile phone cover—in other words, when the view of FIG. 12 is considered as viewed directly from above the screen side. This allows at least some functions of the mobile phone 108 to be used normally.

The mobile phone cover includes a retaining surface comprising the two or more charging stations 110. As depicted in the example of FIG. 1 and FIG. 12, this is the upper surface of the portable charging device 106.

In general:
- the holder 120 comprises one or more mobile phone 108 retainers, configured and arranged to releasably receive and retain the mobile phone 108 such that the visibility of at least a portion of the mobile phone cover is restricted when the mobile phone 108 is retained in the holder 120; and
- one or more rechargeable instrument 104 retainers, configured and arranged to releasably receive and retain the one or more rechargeable instruments 104 in a charging station 110, wherein the one or more charging stations 110 are comprised in the restricted visibility portion of the mobile phone cover such that the visibility of the retained rechargeable instruments 104 is restricted when the mobile phone 108 is retained in the holder 120.

In the example of FIG. 1 and FIG. 12, the holder 120 provides two holding functions 120*a*, 120*b*:

holder 120*a*=configured and arranged to releasably receive and retain the mobile phone 108 (for example, by using one or more mechanical retainers), and holder 120*b*=configured and arranged to be releasably retained by the retaining surface of the portable charging device 106 (for example, by using one or more magnets).

As depicted, the mobile phone 108 is retained in the holder 120*a* when holder 120*b* is released from the mobile phone cover.

Alternatively, the holder 120 may be integrated with the retaining (upper) surface of the portable charging device 106 to provide one holding function. The mobile phone 108 is then released from the holder 120 when it is released from the mobile phone cover.

When the mobile phone 108 is retained in the mobile phone cover, visibility of a portion of the upper surface of the charging device 106 is restricted, and the charging stations 110 are comprised in the portion with restricted visibility. In other words, the mobile phone 108 covers the accessible part of the two or more charging stations 110 when it is retained in the mobile phone cover. The approximate locations of the charging stations 110 covered by the mobile phone 108 are depicted in FIG. 12.

Many different types of retainer configurations which may be used, allowing a higher or lower degree of release. For example, the holder 120 may be configured and arranged to slide over the retention surface to reveal the charging stations 110. Additionally or alternatively, one or more rotation points may be used. Additionally or alternatively, one or more hinges may be used.

Optionally, different degrees of release may be provided, allowing one or more charging stations 110 to be revealed.

Preferably, the visibility of substantially all outer surfaces of the two or more rechargeable instruments 104 is restricted when the mobile phone 108 is retained in the mobile phone cover by being retained in the holder 120.

This provides a very high degree of discretion as the rechargeable instruments 104 are hidden, allowing the user to transport them covertly.

The mobile phone cover providing charging and storage as depicted in FIG. 1, may be further configured and arranged to comprise any of the portable charging devices disclosed herein, such as the depicted embodiments 1106 in FIG. 9, 2106 in FIG. 10, and 3106 in FIG. 11. The relative positions of the retained mobile phone 108 and retained rechargeable instruments 104 may be configured and arranged depending on the requirements of the charging circuits 400, 1400, 2400, 3400. For example, when implementing the example of FIG. 11, it may be advantageous to minimise the distance between energy transfer coil 3125 comprised in the mobile phone and the energy receiving coils 3115 comprised in the two or more rechargeable instruments 104.

Figure 13:
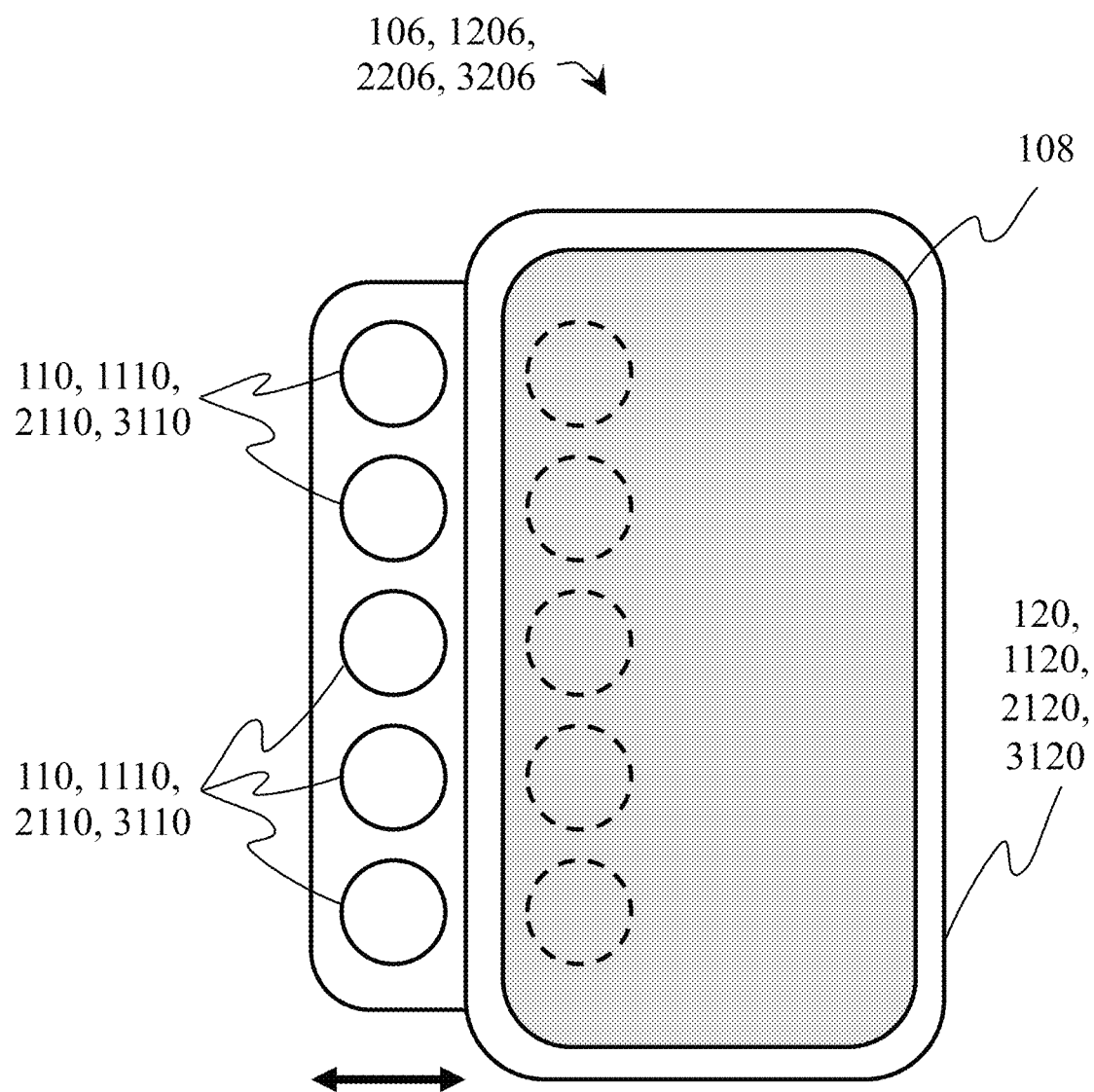
FIG. 13 depicts schematically a further mobile phone cover with discreet storage of one or more rechargeable instruments.

FIG. 13 depicts a portion of a further embodiment of a mobile phone cover schematically after the mobile phone 108 has been placed in a holder 120, 1120, 2120, 3120. FIG. 13 shows the holder 120, 1120, 2120, 3120 portion of the mobile phone cover as viewed from directly above the screen side or the back side of the mobile phone 108. The mobile phone cover includes a retaining surface comprising the two or more charging stations 110, 1110, 2110, 3110. This is the upper surface of the portable charging device 106, 1106, 2106, 3106.

It is the same as depicted in FIG. 12, except:

the portable charging device 106, 1106, 2106, 3106 further comprises one or more drawers, allowing one or more charging stations 110, 1110, 2110, 3110 to be revealed without releasing the mobile phone 108. As depicted, a single drawer is used to reveal and/or cover (conceal) four charging stations 110, 1110, 2110, 3110, but any suitable number of drawers may be used. It may be advantageous to provide one drawer for each charging station 110, 1110, 2110, 3110.

Figure 14:
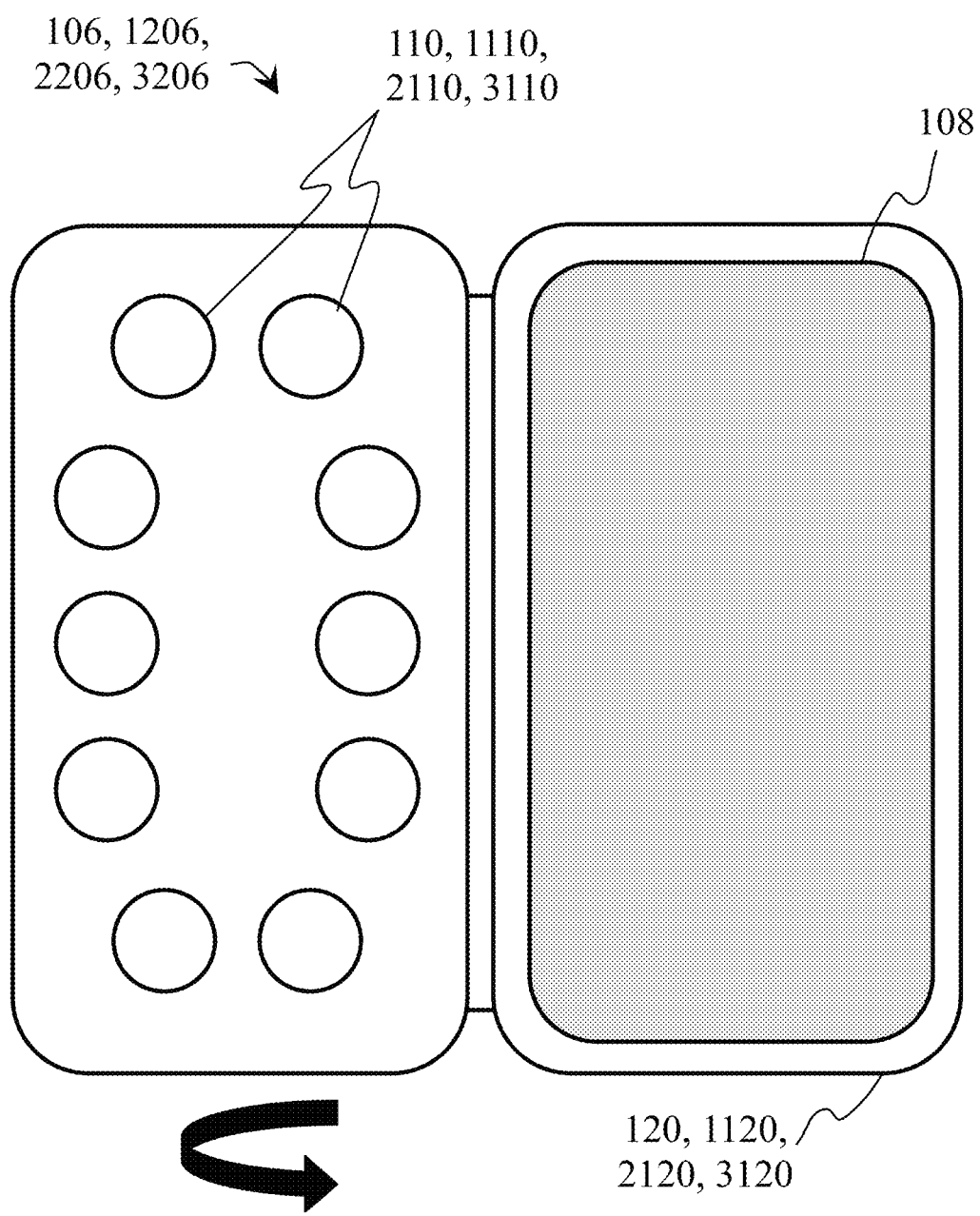
FIG. 14 depicts a portion of a further embodiment of a mobile phone cover schematically after the mobile phone has been placed in a holder

FIG. 14 depicts a portion of a further embodiment of a mobile phone cover schematically after the mobile phone 108 has been placed in a holder 120, 1120, 2120, 3120. FIG. 14 shows the mobile phone cover as viewed from directly above the screen side or the back side of the mobile phone 108. The mobile phone cover comprises two main sections:

a holder 120, 1120, 2120, 3120 portion for retaining the mobile phone 108, depicted on the right, and the charging station 110, 1110, 2110, 3110 portion of the portable charging device 106, 1106, 2106, 3106, depicted on the left.

As depicted, the mobile phone cover is open. These sections are connected using one or more hinges, and the mobile phone cover is closed by rotating the charging station section about the one or more hinges.

In this example, one or more charging stations 110, 1110, 2110, 3110 may be at least partially visible when the mobile phone cover is open. In this example, the visibility of the retained rechargeable instruments 104 is restricted when the mobile phone 108 is retained in the holder 120, 1120, 2120, 3120 and the mobile phone cover is closed.

Optionally, the holder 120, 1120, 2120, 3120 may be further configured and arranged to provide a second holding function, namely to receive and hold the mobile phone cover closed.

While the invention has been described in terms of several embodiments, it is contemplated that alternatives, modifications, permutations and equivalents thereof will become apparent to those skilled in the art upon reading the specification and upon study of the drawings. It must be understood that this description is given solely by way of example and not as limitation to the scope of protection, which is defined by the appended claims.

For example, it may be advantageous for the mobile phone cover to further comprise one or more software, mechanical, electrical, optical or acoustic elements to indicate to a user that one or more rechargeable instruments 104 are retained in a charging station 110, 1110, 2110, 3110. Additionally or alternatively, an empty charging station 110, 1110, 2110, 3110 may also be similarly indicated. It may be advantageous for the occupancy status of the charging stations to be indicated using a software app, running on the mobile phone 108.

Additionally or alternatively, it may be advantageous for the mobile phone cover to further comprise one or more software, mechanical, electrical, optical or acoustic elements to indicate to a user the charging states of one or more rechargeable instruments 104 retained in a charging station 110, 1110, 2110, 3110. Additionally or optionally, the discharge state and/or estimated usage time may also be similarly indicated. It may be advantageous for the charge/ discharge/usage status of the rechargeable instruments 104 to be indicated using a software app, running on the mobile phone 108.

Optionally, the charging stations may be further configured and arranged to allow convenient cleaning by a user. This is particularly advantageous when the rechargeable instruments 104 are configured for use, either directly or indirectly, in one or more therapeutic, stimulation and/or medical uses.

In a further example, a mobile phone cover may comprise:
- a holder 120, 1120, 2120, 3120 for receiving and retaining a mobile phone 108;
- portable charging device 106, 1106, 2106, 3106 having two or more charging stations 110, 1110, 2110, 3110 and an energy supply, each charging station 110, 1110, 2110, 3110 being configured and arranged for receiving and retaining a rechargeable instrument 104, the rechargeable instrument 104 comprising an energy storage;
- the portable charging device 106, 1106, 2106, 3106 being further configured and arranged:
  - to transfer energy, in use, from the energy supply of portable charging device 106, 1106, 2106, 3106 to the two or more charging stations 110, 1110, 2110, 3110; and
  - to transfer energy, in use, from the charging stations 110, 1110, 2110, 3110 to the energy storage of the rechargeable instrument 104 placed in the respective charging station 110, 1110, 2110, 3110.

By providing an energy supply in the portable charging station, this may further reduce the risk that the instruments 104 will not work properly or be inoperable when the user requires it. The rechargeable instrument 104 should not be construed as including one or more mobile phones 108.

Alternatively, the energy supply of the portable charging device 106, 1106, 2106, 3106 may comprise one or more rechargeable batteries. This may allow the portable charging device 106, 1106, 2106, 3106 to be charged by an external charging device. In this example, the external charging device should not be construed, in this example, as including the mobile phone to be received and retained in the mobile phone cover.

In a further example, any of the mobile phone covers described herein may have a first and second outer surface, extended longitudinally and extended transversely, the thickness being determined by a perpendicular distance between corresponding points on the first and second outer surfaces, the mobile phone cover having a maximum thickness of 2 cm or less, preferably 1 cm or less, more preferably 0.5 cm or less.

There is a growing need to transport smaller instruments, particularly when these are personalised. A thinner-dimensioned cover may mean that the user is more likely to use the cover regularly, preferably every day. It may also further increase portability.

The invention claimed is:

1. A mobile phone cover comprising:
  a holder for receiving and retaining a mobile phone, the mobile phone comprising an energy supply;
  a portable charging device having two or more charging stations, each charging station being configured and arranged for receiving and retaining a rechargeable medical instrument, the rechargeable instrument comprising an energy storage;
  the portable charging device being further configured and arranged:
    to transfer energy, in use, from the energy supply of the mobile phone, placed in the holder, to the two or more charging stations; and
    to transfer energy, in use, from the charging stations to the energy storage of the rechargeable instrument placed in the respective charging station.

2. The mobile phone cover according to claim 1, wherein one or more rechargeable instruments are a wearable device, a cosmetic device, a device configured for powering a further device, a device configured for powering wirelessly a further device, a device configured for powering a further rechargeable instrument, a device configured for powering wirelessly a further rechargeable instrument, or are a companion device for an implantable device, an implantable neurostimulation device, an EPTD, a medical device, an implantable medical device (IMD), a therapeutic device, a medical aid, a device for stimulating one or more nerves (neurostimulator), a device for stimulating one or more muscles, a device for stimulating one or more organs, a device for stimulating spinal cord tissue, or any combination thereof.

3. The mobile phone cover according to claim 1, wherein the two or more charging stations are further configured and arranged to retain the rechargeable instruments using:
  one or more magnets, one or more mechanical retainers, one or more protrusions, one or more recesses, one or more fasteners, one or more openings, one or more resilient elements, one or more elastic elements, one or more clamps, one or more hooks, one or more threaded elements, one or more pins, one or more adhesive elements, one or more coating, and any combination thereof.

4. The mobile phone cover according to claim 1, wherein the energy storage of one or more rechargeable instruments comprises one or more rechargeable batteries.

5. The mobile phone cover according to claim 1, wherein the energy supply of the mobile phone comprises one or more rechargeable batteries.

6. The mobile phone cover according to claim 1, wherein the portable storage device comprises a further energy storage, comprising one or more rechargeable batteries.

7. The mobile phone cover according to claim 1, wherein the holder is further configured and arranged to retain the mobile phone using:
  one or more magnets, one or more mechanical retainers, one or more protrusions, one or more recesses, one or more fasteners, one or more openings, one or more resilient elements, one or more elastic elements, one or more clamps, one or more hooks, one or more threaded elements, one or more pins, one or more adhesive elements, one or more coating, and any combination thereof.

8. The mobile phone cover according to claim 1, wherein the portable charging device further comprises one or more electrical interconnections and/or electrical connector.

9. The mobile phone cover according to claim 1, wherein the portable charging device further comprises one or more electrical components, configured and arranged to control charging in use.

10. The mobile phone cover according to claim 9, wherein the one or more electrical components comprise one or more rechargeable batteries.

11. The mobile phone cover according to claim 9, wherein the one or more electrical components comprise one or more coils, configured and arranged to transmit and/or receive energy wirelessly.

12. The mobile phone cover according to claim 1, wherein one or more rechargeable instruments comprise a further energy supply;
   the portable charging device being further configured and arranged:
      to transfer energy, in use, from the further energy supply of the one or more rechargeable instruments placed in a first charging station, to one or more further charging stations; and
      to transfer energy, in use, from the one or more further charging stations to the energy storage of the rechargeable instrument placed in the respective further charging station.

13. The mobile phone cover according to claim 1, wherein the portable charging device is further configured and arranged, in use:
   to transfer data from the mobile phone to one or more rechargeable instrument;
   to receive data by the one or more rechargeable instrument from the mobile phone;
   to transfer data from one or more rechargeable instrument to the mobile phone;
   to receive data by the mobile phone from the one or more rechargeable instrument;
   to transfer data from a first rechargeable instrument to a further rechargeable instrument;
   to receive data by a further rechargeable instrument from the one or more rechargeable instrument;
   and any combination thereof.

14. The mobile phone cover according to claim 13, wherein:
   the rechargeable instrument comprises a memory configured for storing a device parameter set of data;
   the portable charging device is further configured to detect placement in a charging station, and to transmit the device parameter set stored in its memory to the portable charging device.

15. The mobile phone cover according to claim 13, wherein the portable charging device further comprises one or more memory components, configured and arranged to store and/or distribute one or more parameter sets of data.

16. The mobile phone cover according to claim 15, wherein the portable charging device is further configured:
   to receive the device parameter set of data from a rechargeable instrument placed in a charging station; and
   to store the device parameter set of data in the memory of the portable charging device.

17. The mobile phone cover according to claim 16, wherein the portable charging device is further configured:
   after receipt of the device parameter set, to transmit all device parameter sets stored in the memory of the portable charging device to rechargeable instruments placed in a charging station.

18. The mobile phone cover according to claim 16, wherein:
   each device parameter set further comprises a time stamp; and
   the portable charging device is further configured to replace a device parameter set with a specific unique identification code stored in its memory with a device parameter set with the same specific unique identification code received from a rechargeable instrument when the time stamp of the parameter set with the specific unique identification code stored in its memory indicates a time which is prior to time indicated by the time stamp of the parameter set with the same specific unique identification code received from the rechargeable instrument.

19. The mobile phone cover according to claim 13, wherein the data transfer occurs at least partially according to a protocol selected from:
   Bluetooth, Bluetooth LE, NFC, Low-power WAN, LTE, Qi, Wi-Fi, and any combination thereof.

20. The mobile phone cover according to claim 1, wherein:
   the holder comprises one or more mobile phone retainers, configured and arranged to releasably receive and retain the mobile phone such that the visibility of at least a portion of the mobile phone cover is restricted when the mobile phone is retained in the holder;
   one or more rechargeable instrument retainers, configured and arranged to releasably receive and retain the one or more rechargeable instruments in a charging station, wherein the one or more charging stations are comprised in the restricted visibility portion of the mobile phone cover such that the visibility of the retained rechargeable instruments is restricted when the mobile phone is retained in the holder.

21. The mobile phone cover according to claim 20, wherein the visibility of substantially all outer surfaces of the rechargeable instruments is restricted when the mobile phone is retained in the holder.

22. The mobile phone cover according to claim 20, wherein the visibility of the retained rechargeable instruments is restricted when the mobile phone is retained in the holder and the mobile phone cover is closed.

23. The mobile phone cover according to claim 1, wherein energy transfer occurs at least partially according to a protocol selected from:
   Qi, Powermat, Rezence, WiPower, Open Dots, PMA, Wireless Power Transfer (WPT), Simultaneous Wireless Information and Power Transfer (SWIPT), inductive coupling, resonant inductive coupling, capacitive coupling, and any combination thereof.

24. The mobile phone cover according to claim 1, wherein one or more rechargeable instruments are a personalized device, a custom-made device, a device for an individual, a patient-specific device, a patient-adaptable device, or any combination thereof.

25. A medical system comprising N implantable medical devices (IMD); a mobile phone cover according to claim 1, and M rechargeable instruments, wherein M≥N≥2, a rechargeable instrument is configured for powering wirelessly an implantable medical device (IMD) and comprises a memory configured for storing an implantable device parameter set of data, wherein:
   the memory is configured for storing at least N implantable device parameter sets, each of the at least N implantable device parameter sets comprises a unique identification code and wherein the rechargeable instrument is configured to transmit wirelessly implantable device parameter sets;
   an IMD comprises a unique IMD identification code and is configured to receive wirelessly at least the implantable device parameter set which unique identification code matches its unique IMD identification code and to deploy said parameter set to enable the IMD to provide the corresponding electrical stimulation to the tissue where the IMD is inserted.

26. The medical system according to claim 25, wherein the rechargeable instruments are external power transfer devices (EPTD).

27. The mobile phone cover according to claim 1, wherein the mobile phone cover has a first and second outer surface, extended longitudinally and extended transversely, the thickness being determined by a perpendicular distance between corresponding points on the first and second outer surfaces, the mobile phone cover having a maximum thickness of 2 cm or less, preferably 1 cm or less, more preferably 0.5 cm or less.

28. A mobile phone cover comprising:
- a holder for receiving and retaining a mobile phone;
- a portable charging device having two or more charging stations and an energy supply, each charging station being configured and arranged for receiving and retaining a rechargeable instrument, the rechargeable instrument comprising an energy storage;
- the portable charging device being further configured and arranged:
  - to transfer energy, in use, from the energy supply of portable charging device to the two or more charging stations; and
  - to transfer energy, in use, from the charging stations to the energy storage of the rechargeable instrument placed in the respective charging station.

29. The mobile phone cover according to claim 28, wherein the energy supply of the portable charging device comprises one or more rechargeable batteries.

30. The mobile phone cover according to claim 28, wherein the mobile phone cover has a first and second outer surface, extended longitudinally and extended transversely, the thickness being determined by a perpendicular distance between corresponding points on the first and second outer surfaces, the mobile phone cover having a maximum thickness of 2 cm or less, preferably 1 cm or less, more preferably 0.5 cm or less.

* * * * *